US008536146B2

(12) United States Patent
Eberwine et al.

(10) Patent No.: US 8,536,146 B2
(45) Date of Patent: Sep. 17, 2013

(54) CYTOPLASMIC BK$_{Ca}$ CHANNEL INTRON-CONTAINING MRNAS CONTRIBUTE TO THE INTRINSIC EXCITABILITY OF HIPPOCAMPAL NEURONS

(75) Inventors: James Eberwine, Philadelphia, PA (US); Jai-Yoon Sul, Bensalem, PA (US); Thomas J. Bell, Turnersville, NJ (US); Kevin Miyashiro, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 353 days.

(21) Appl. No.: 12/597,460
(22) PCT Filed: Apr. 25, 2008
(86) PCT No.: PCT/US2008/005413
§ 371 (c)(1),
(2), (4) Date: Apr. 27, 2010
(87) PCT Pub. No.: WO2008/134027
PCT Pub. Date: Nov. 6, 2008

(65) Prior Publication Data
US 2010/0203629 A1 Aug. 12, 2010

Related U.S. Application Data

(60) Provisional application No. 60/926,327, filed on Apr. 25, 2007.

(51) Int. Cl.
*C12N 15/11* (2006.01)
*C12N 5/00* (2006.01)
(52) U.S. Cl.
USPC .......................................... 514/44 A; 435/326
(58) Field of Classification Search
USPC ........................................ 435/326; 514/44 A
See application file for complete search history.

(56) References Cited

U.S. PATENT DOCUMENTS
2003/0162734 A1   8/2003   Miller et al.
2004/0009497 A1   1/2004   Kandel et al.

OTHER PUBLICATIONS

Atkinson et al., "A component of calcium-activated potassium channels encoded by the *Drosophila slo* locus" (1991) *Science* 253:551-555.
Butler et al., "mSlo, a complex mouse gene encoding "Maxi" calcium-activated potassium channels" (1993) *Science* 261:221-224.
Chen et al., "Functionally diverse complement of large conductance calcium- and voltage-activated potassium channel (BK) α-subunits generated from a single site of splicing" (2005) *JBC* 280:33599-33609.
Chen et al., "Deletion of *Kv4.2* gene eliminates dendritic A-type K$^+$ current and enhances induction of long-term potentiation in hippocampal CA1 pyramidal neurons" (2006) *J. Neurosci* 26:12143-12151.
Du et al., "Calcium-sensitive potassium channelopathy in human epilepsy and paroxysmal movement disorder" (2005) *Nat. Genet.* 37:733-738.
Fettiplace et al., "Mechanisms of hair cell tuning" (1999) *Annual Rev. Physiol.* 61:809-834.
Gulledge et al., "Synaptic integration in dendritic trees" (2005) *Journ. of Neurobiol.* 64:75-90.
Ikeda et al., "Variability of β-amyloid protein deposited lesions in down's syndrome brains" (1994) *J Exp Med.* 174:189-198.
Isbrandt et al., "Gene structures and expression profiles of three human KCND (Kv4) potassium channels mediating A-type currents I(TO) and I(SA)" (2000) *Genomics* 64:144-154 (Abstract Only).
Johnston et al., "Potassium channels and dendritic function in hippocampal pyramidal neurons" (2000) *Epilepsia* 41:1072-1073.
Kalcheva et al., "Genomic structure of human microtubule-associated protein 2 (MAP-2) and characterization of additional MAP-2 isoforms" (1995) *PNAS* 92:10894-10898.
Konig et al., "Splicing segregation: the minor spliceosome acts outside the nucleus and controls cell proliferation" (2007) *Cell* 131:718-729.
Kwon et al., "Multiple sequences in the C terminus of MaxiK channels are involved in expression, movement to the cell surface, and apical localization" (2004) *PNAS* 101:15237-15242.
Laumonnier et al. "Association of a functional deficit of the BK$_{Ca}$ channel, a synaptic regulator of neuronal excitability, wth autism and mental retardation" (2006) *Am J Psychiatry* 163:1622-1629.
Li et al., "An intron with a constitutive transport element is retained in a Tap messenger RNA" (2006) *Nature* 443:234-237 (Abstract Only).
Liu et al., "Cloning and characterization of glioma BK, a novel BK channel isoform highly expressed in human glioma cells" (2002) *J Neurosci* 22:1840-1849.
MacDonald et al., "Increased large conductance calcium-activated potassium (BK) channel expression accompanied by STREX variant downregulation in the developing mouse CNS" (2006) *BMC Dev Biol.* 27:37-47.
Nadal et al., "Differential characterization of three alternative spliced isoforms of DPPX" (2006) *Brain Res.* 1094:1-12 (Abstract Only).
Navaratnam et al., "Differential distribution of Ca$^{2+}$-activated K$^+$ channel splice variants among hair cells along the tonotopic axis of the chick cochlea" (1997) *Neuron* 19:1077-1085.
Poolos et al., "Calcium-activated potassium conductances contribute to action potential repolarization at the soma but not the dendrites of hippocampal CA1 pyramidal neurons" (1999) *J. Neurosci* 19:5205-5212.
Rockenstein et al., "Levels and alternative splicing of amyloid β protein precursor (APP) transcripts in brains of APP transgenic mice and humans with alzheimer's disease" (1995) *JBC* 270:28257-28267.
Rosenblatt et al., "Distribution of Ca$^{2+}$-activated K$^+$ channel isoforms along the tonotopic gradient of the chicken's cochlea" (1997) *Neuron* 19:1061-1075.
Ruttiger et al., "Deletion of the Ca$^{2+}$-activated potassium (BK) α-subunit but not the BKβ1-subunit leads to progressive hearing loss" (2004) *PNAS* 101:12922-12927.
Salkoff et al., "High-conductance potassium channels of the SLO family" (2006) *Nature Reviews* 5:921-931.
Sausbier et al., "Cerebellar ataxia and purkinje cell dysfunction caused by Ca$^{2+}$-activated K$^+$ channel deficiency" (2004) *PNAS* 101:9474-9478.
Sausbier et al., "Elevated blood pressure linked to primary hyperaldosteronism and impaired vasodilation in BK channel-deficient mice" (2005) *Circulation* 112:60-68.
Shipston, M.J., "Alternative splicing of potassium channels: a dynamic switch of cellular excitability" (2001) *Trends Cell Biol.* 11:353-358.
Tseng-Crank et al., "Cloning, expression, and distribution of functionally distinct Ca$^{2+}$-activated K$^+$ channel isoforms from human brain" (1994) *Neuron.* 13:1315-1330.
Zarei et al., "An endoplasmic reticulum trafficking signal prevents surface expression of a voltage- and Ca$^{2+}$-activated K$^+$ channel splice variant" (2004), *PNAS* 101:10072-10077.

*Primary Examiner* — J. E. Angell

(74) *Attorney, Agent, or Firm* — Riverside Law LLP

(57) ABSTRACT

The invention relates to a method of modulating neuronal function by modulating the cytoplasmic level in a neuron of an intron-containing mRNA. The methods are useful in diagnostic, research and therapeutic applications.

8 Claims, 12 Drawing Sheets

Figures 1F-1H
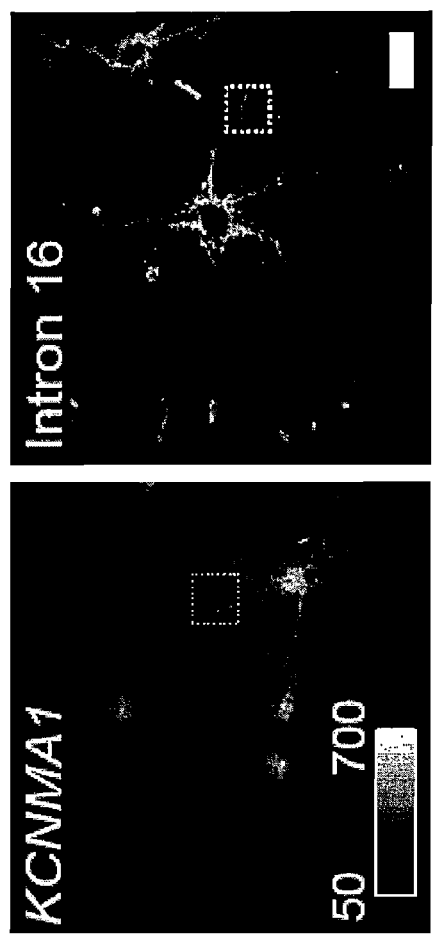
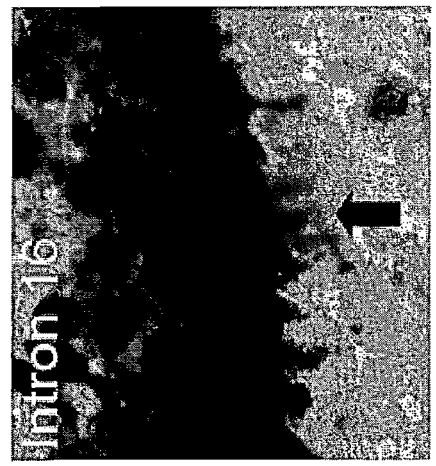
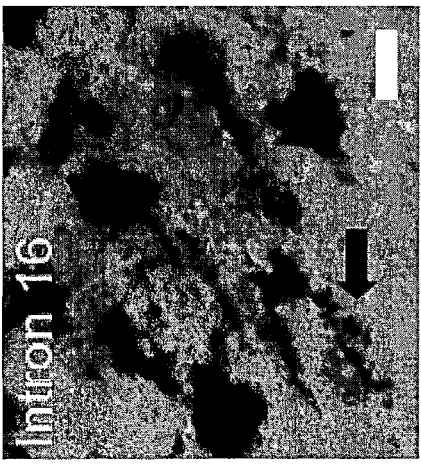
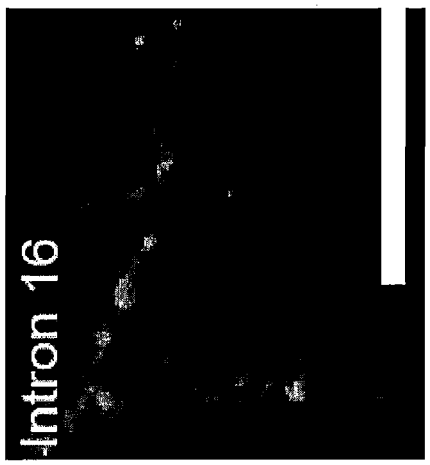
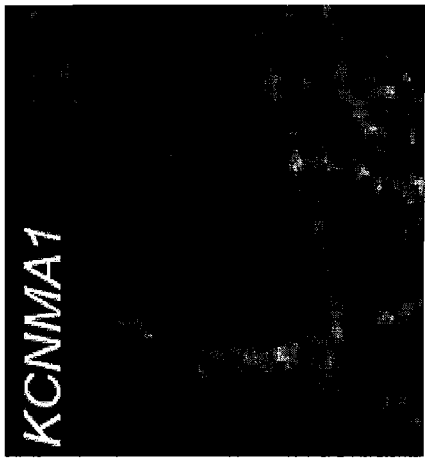

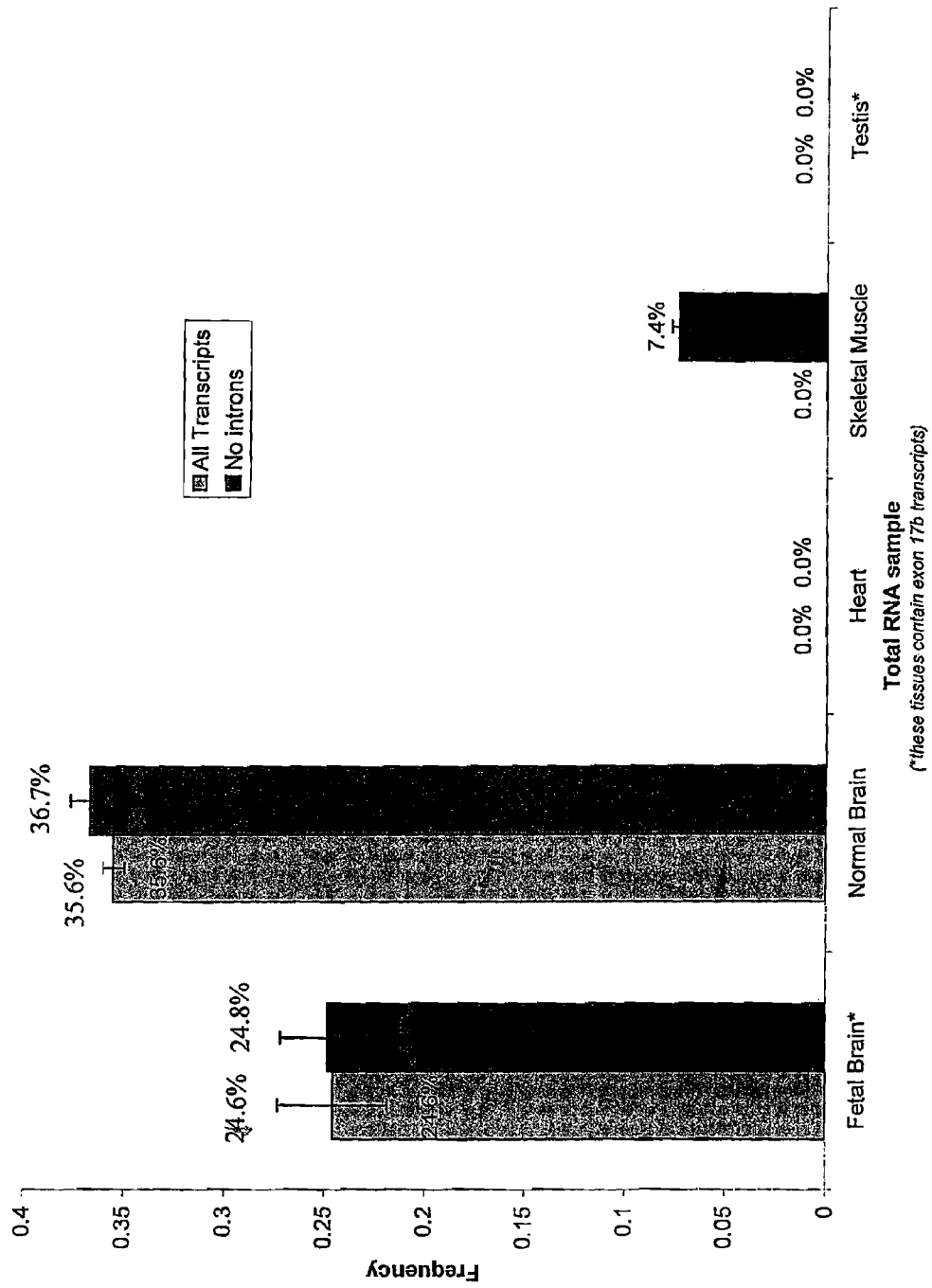

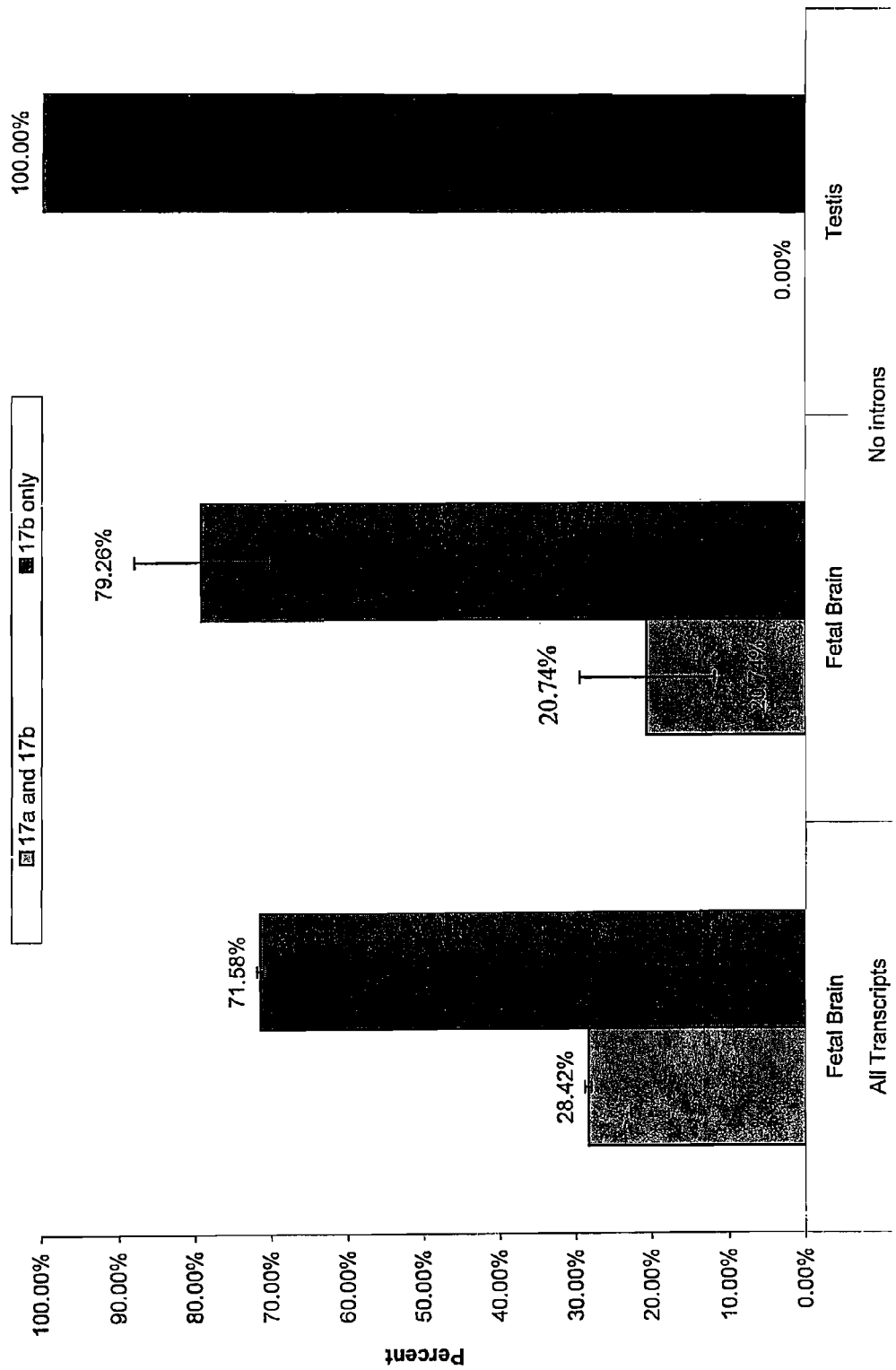

CYTOPLASMIC BK$_{Ca}$ CHANNEL INTRON-CONTAINING MRNAS CONTRIBUTE TO THE INTRINSIC EXCITABILITY OF HIPPOCAMPAL NEURONS

STATEMENT REGARDING FEDERALLY SPONSORED RESEARCH OR DEVELOPMENT

This invention was supported in part by funds obtained from the U.S. Government (National Institutes of Health grant numbers AG9900 and MH58371), and the U.S. Government therefore has certain rights in the invention.

CROSS-REFERENCE TO RELATED APPLICATIONS

This is a National Stage application of PCT International Application No. PCT/US2008/005413, filed Apr. 25, 2008, which in turn claims the benefit pursuant to 35 U.S.C. §119(e) of U.S. Provisional Application No. 60/926,327, filed on Apr. 25, 2007, which is hereby incorporated by reference in its entirety herein.

BACKGROUND OF THE INVENTION

Each neuron is comprised of a nucleus within a body, or soma, a long fiber called the axon, and a varying number of branching fibers called dendrites, which extend out to other neurons. A single neuron can make numerous contacts with other neurons and tissues. For example, every new thought process is handled by a new set of synaptic connections. Memory itself is a set of synaptic connections engraved in the network of neurons.

Dendrites are specialized extensions of the neuronal soma that contain components of the cellular machinery involved in RNA and protein metabolism, as well as a distinctive set of mRNAs. Increasingly, more detailed molecular analyses of dendrites have shown that a subset of cellular RNAs are transported into dendrites where they can be translated into protein at specialized areas following synaptic stimulation (Aakalu et al., 2001, Neuron 30:489-502; Bassell et al., 1998, J. Neurosci. 18:251-65; Crino et al., 1996, Neuron 17:1173-87; Huber et al., 2000, Science 288:1254-7; Job et al., 2001, Proc. Natl. Acad. Sci. U.S.A 98:13037-42; Martin et al., 1997, Cell, 91:927-38). Several of these mRNAs play central roles in synaptic transmission.

In mammalian neurons, the firing of an action potential requires the coordinated gating of at least a dozen different classes of voltage-gated ion channels. The integration of these currents manifests itself as characteristic input-output properties intrinsic to each neuron. One such firing property of some neurons, such as those in the hippocampus (Gu et al., 2007, J Physiol 580(Pt.3):859-82. Epub 2007 Feb. 15; Lancaster et al., 1987, The Journal of Physiology 389: 187-203; Storm, J. F., 1987, The Journal of Physiology 385: 733-759) or cerebellum (Callaway et al., 1997, Journal of Neurophysiology 77: 145-152; Cavelier et al., 2002, The Journal of Physiology 540: 57-72), is the ability to initiate repetitive burst firing in response to depolarizing current. Voltage clamp analysis suggests that the small net inward current that drives the depolarizing momentum is a result of a subtle balance of the sum of inward and outward postspike currents (Swensen et al., 2003, J Neurosci 23: 9650-9663). Although short-term and long-term feedback mechanisms exist to preserve burst firing (Swensen et al., 2005, J Neurosci 25: 3509-3520), it is known that relatively small changes in the size of an individual current may have a dramatic impact on firing activity (Burdakov et al., 2002, J Neurosci 22: 6380-6387).

One transient current activated during the falling phase of the action potential is the BK$_{Ca}$ channel. In the central nervous system, BK$_{Ca}$ channels are localized to the cell soma as well as the pre- and post-synaptic terminals of neurons where they regulate fundamental neuronal functions such as burst firing, neurotransmitter release, shaping action potential waveforms, and frequency tuning (Salkoff et al., 2006, Nature Reviews 7: 921-931). Native channels are assembled as tetramers of the pore-forming α-subunits encoded by a single gene, KCNMA1 (previously called slo-1), (Atkinson et al., 1991, Science 253: 551-555; Butler et al., 2003, Science 261: 221-224). This gene is subject to vast tissue—(Tseng-Crank et al., 1994, Neuron 13: 1315-1330) and cell-specific alternative splicing (Navaratnam et al., 1997, Neuron 19: 1077-1085; Rosenblatt et al., 1997, Neuron 19: 1061-1075). The resulting functional heterogeneity in BK$_{Ca}$ channel currents is due in part to these splicing events generating BK$_{Ca}$ channels with altered Ca$^{2+}$-sensitivity and gating kinetics for (review see Salkoff et al., 2006, Nature Reviews 7: 921-931; Shipston, M. J., 2001, Trends Cell Biol 11: 353-358), as well as altered channel trafficking (Kwon et al., 2004, Proceedings of the National Academy of Sciences of the United States of America 101: 15237-15242; Zarei et al., 2004, Proceedings of the National Academy of Sciences of the United States of America 101: 10072-10077). Channel differences also arise from modulation via a family of tissue-specific auxiliary β-subunits (Fettiplace et al., 1999, Annu Rev Physiol 61: 809-834).

Currently, the functional diversity among BK$_{Ca}$ channels in neurons is not fully resolved, but the expression and subcellular distribution patterns of splice variants are expected to be one functionally significant factor in determining their characteristic input-output properties. Indeed, some K$^+$ channels, for example BK$_{Ca}$ (Poolos et al., 1999, Neurosci 19: 5205-5212) or A-type (Colbert et al., 1999, J Neurosci 19: 8163-8171; Hoffman et al., 1998, J Neurosci 18: 3521-3528), establish functional gradients within the dendritic processes of mature neurons where they transform the shape of local synaptic potentials or size of somatic action potentials (Gulledge et al., 2005, Journal of Neurobiology 64: 75-90; Johnston et al., 2000, Epilepsia 41: 1072-1073).

A mutation in the gene encoding the pore-forming subunit of BK$_{Ca}$ channels has been linked to a variety of human diseases, including autism (Laumonnier et al., 2006, Am J Psychiatry 163:1622-1629), coexistent generalized epilepsy and paroxysmal dyskinesia (Du et al., 2005, Nat Genet. 37: 733-738). In genetic studies, mice lacking the KCNMA1 gene display several dysfunctions, such as progressive hearing loss, cerebellar ataxia, elevated blood pressure and reduced burst firing in cerebellar Purkinje neurons (Sausbier et al., 2005, Circulation 112:60-68; Sausbier et al., 2004, PNAS 101: 9474-9478; Ruttiger et al., 2004, PNAS 101: 12922-12927). Changes in BK channel expression levels have also been associated with multiple clinical disorders in humans. The expression levels of BK channels are elevated in human glioma biopsies; the increase expression of the BK channels correlates directly to malignancy grade of the tumor (Liu et al., 2002, J Neurosci 22:1840-1849; Weaver et al., 2004, J Neurosci Res 78:224-234). In ageing human coronary smooth muscle, the expression levels of BK channels are greatly reduced (Marie et al., 2001). The decrease in BK channels expression is believed to increase the risk of coronary spasm and myocardial ischemia in older people.

Despite the existing knowledge in the art about the significant clinical and functional roles associated with BK channels and other neuronal proteins, the functional significance of mRNA isoforms encoding these neuronal proteins has not been addressed. Thus, there is a need in the art for a better understanding of the function and role of mRNA isoforms in order to facilitate the study, diagnosis and therapeutic treatment of pathologies of neurons. This invention addresses that need.

BRIEF SUMMARY OF THE INVENTION

The invention provides a method for modulating the excitability of a neuron. The method comprises the step of modulating the cytoplasmic level in a neuron of an intron-containing KCNMA1 mRNA, wherein said modulation in the cytoplasmic level of the intron-containing KCNMA1 mRNA modulates the excitability of the neuron, wherein a decrease in the cytoplasmic level of the intron-containing KCNMA1 mRNA causes a decrease in the excitability of said neuron. In an embodiment, the in intron-containing KCNMA1 mRNA comprises intron 16. The intron 16-containing KCNMA1 mRNA may further comprise exon 17 spliced directly to exon 18.

In one aspect, the modulating step comprises decreasing the cytoplasmic level of the intron-containing KCNMA1 mRNA. In an embodiment, the cyptoplasmic level is decreased by administering siRNA molecules to the neuron. In another embodiment, the cytoplasmic level is decreased by increasing splicing of the intron-containing mRNA. In some embodiments, decreasing the cytoplasmic level of the intron-containing KCNMA1 causes a change in distribution of $BK_{Ca}$ channels in the neuron.

In another aspect, the modulating step comprises increasing the cytoplasmic level of the intron-containing KCNMA1 mRNA. In one embodiment, increasing the cytoplasmic level of the intron-containing KCNMA1 mRNA comprises decreasing splicing of the intron-containing mRNA. In another embodiment, the modulating step comprises providing exogenous intron-containing KCNMA1 mRNA to the neuron, thereby increasing the cytoplasmic level of the intron-containing KCNMA1 mRNA.

The invention further provides a method for modulating the function of a neuron. The method comprises the step of modulating the cytoplasmic level in a neuron of an intron-containing mRNA by increasing or decreasing splicing of the intron-containing mRNA, wherein the modulation in the cytoplasmic level of an intron-containing mRNA modulates the function of the neuron. In one embodiment, the intron-containing mRNA is dendritically targeted.

In one embodiment, the intron-containing mRNA is selected from the group consisting of an intron-containing KCNMA1 mRNA, an intron-containing amyloid beta precursor (AMB4) mRNA, an intron-containing potassium channel Kv4.2 (Kv4.2) mRNA, and an intron-containing microtubule-associated protein-2 (MAP2) mRNA.

In an embodiment, the intron-containing AMB4 mRNA comprises at least one of intron 6 and intron 17. In another embodiment, the intron-containing Kv4.2 mRNA comprises at least one of intron 1 and intron 4. In yet another embodiment, the intron-containing MAP2 mRNA comprises at least one of intron 3 and intron 4.

In one aspect, the modulating step comprises reducing the cytoplasmic level of the intron-containing mRNA by administering siRNA molecules to the neuron, thereby decreasing splicing indirectly by reducing the amount of splicing substrate.

Further provides is a method for modulating the function of a cell. The method comprises the step of modulating the cytoplasmic level in a cell of an intron-containing mRNA by increasing or decreasing splicing of the intron-containing mRNA, wherein the cell is selected from the group consisting of heart, testis, brain and skeletal muscle and wherein the modulation in the cytoplasmic level of an intron-containing mRNA modulates the function of the cell.

In an embodiment, the intron-containing mRNA is an intron-containing KCNMA1 mRNA. Preferably, the intron-containing KCNMA1 mRNA comprises intron 16.

In one aspect of the method for modulating the function of a cell, the modulating step comprises decreasing the cytoplasmic level of the intron-containing mRNA. In another aspect, the modulating step comprises increasing the cytoplasmic level of the intron-containing mRNA.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIGS. 1A-1H are a series of images relating to the presence of $BK_{Ca}$ channel intron-containing mRNAs are present in the cytoplasm of hippocampal neurons. FIG. 1A is a schematic illustration of the putative membrane topology of the $BK_{Ca}$ channel α-subunit, and the location of two sites of alternative splicing (black circles). A partial genomic structure of KCNMA1 gene was constructed based upon the public rat genomic sequence (GenBank® accession number NW_043710). Exons are denoted with vertical solid bars (black indicates constitutively exons and gray indicates alternatively spliced exons) and introns with thin horizontal lines. Exon lengths are 69, 12, 87, 77, 9, 174 and 94 nucleotides for e15, e15a, e16, e17, e17a, e17b and e18. Intron lengths are 2,340, 6,222, 6,654, 4,528, 6,421 and 30,920 nucleotides for i15, i15b, i16-containing, i17, i17a, and i17b. FIG. 1B depicts the results of KCNMA1 splice variant analysis performed in hippocampal tissue. For the alternative splice analysis, the "all transcript" produced were analyzed using primers XP1, XP2 and XP3 on two separate hippocampus samples in replicate (n=16). For i16 transcripts, two samples of both hippocampus and hippocampal dendrites were analyzed in replicate (n=2) with XP2 and XP3. FIG. 1C is an image of a gel containing PCR products from an RT-PCR analysis of i16-containing $BK_{Ca}$ channel mRNA in dendrites (n=2). FIG. 1D is a series of images of gels containing PCR products from an RT-PCR analysis of KCNMA1 and i16-containing $BK_{Ca}$ channel mRNA in dendrites (n=2). FIG. 1E is an image of microarray analysis of introns retained in dendritically-localized mRNA. Hybridization results for Cy5-labeled aRNA from mechanically-isolated primary rat hippocampal dendrites. Targeted sequences represent regions of amyloid beta (AMB4) precursor; lane A is intron 1, lane B is intron 6, and lane C is intron 17; potassium channel Kv4.2 (Kv4.2): Lane 1 is intron 1, lane 2 is intron 2, and lane 3 is intron 4; microtubule-associated protein-2 (MAP2): lane 1 is intron 3, lane 2 is intron 4, and lane 3 is intron 12; calcium/calmodulin-dependent protein kinase II (CaMKII): lane 1 is intron 1, lane 2 is intron 3, lane 3 is intron 10. FIG. 1F is an image in situ histochemical analysis of the subcellular localization of KCNMA1 mRNA (e22 to 25) and i16-containing $BK_{Ca}$ channel mRNA (n=3). Anti-digoxigenin Fab fragments conjugated to Qdot-565 were used to enhance the detection and visualization. The upper panels are photomicrograph image of ISH of cultured hippocampal neurons with KCNMA1e22-25 probe, and i16-containing $BK_{Ca}$ channel mRNA probe.

The lower panels are enlargements of the dotted region marked in the upper panels. FIG. 1G is a differential interference contrast (DIC) photomicrograph depicting ISH of the hippocampus of adult rat brain tissue with i16-containing $BK_{Ca}$ channel mRNA probe (n=2). The black arrow highlights positive dendrites. FIG. 1H is a DIC photomicrograph depicting ISH with i16-containing $BK_{Ca}$ channel mRNA probe in the anterior striatum of adult rat brain tissue (n=2). The black arrow highlights positive dendrites. Scale bars=25 µm.

FIG. 2A is an image of data for the KCNMA1 probe and KCl-treated neurons. The insert shows negative control. FIG. 2B is an image for the intron 16 probe and KCl-treated neurons. FIG. 2C is an image of data for the intron 16 probe and KCl- and Nifedipine-treated neurons. FIG. 2D is an image of data for the intron 16 probe and KCl and ω-conotoxin GVIA-treated neurons. FIG. 2E is an image of the intron 16 probe and KCl and ω-conotoxin MVIIC-treated neurons. Scale bars=25 µm. FIG. 2F is an image of PCR products from a RT-PCR analysis used to demonstrate that these pharmacological manipulations did not produce changes in KCNMA1 $BK_{Ca}$ mRNA levels in hippocampal dendrites. Cultured hippocampal neurons were exposed to the depolarizing stimulus and the channel blockers as previously described. Immediately following treatment the dendrites were harvested, subjected to aRNA amplification, and used as a template for RT-PCR analysis.

FIG. 3A is a fluorescence image showing the siRNA-Glo Rhodamine signal in the transfected neurons. FIG. 3B is a photomicrograph that is a merged image of fluorescence signal over DIC image. White arrows indicate sites of fluorescence signal. FIG. 3C is a DIC photomicrograph depicting the ISH staining with i16-containing probe. Insert shows same cell visualized by light microscopy. FIG. 3D is a DIC photomicrograph showing the ISH staining with KCNMA1 e22-25 probe. Insert shows same cell by light microscopy. Scale bars=25 µm. Anti-digoxigenin Fab fragments conjugated to alkaline phosphatase were used for detection of the NBT/BCIP chromogenic substrate.

FIG. 4A is a series of representative action potential traces from 50 nA current injection: FIG. 4B is a histogram summary of the maximum number of action from control, si16-treated, mock, and si16-treated in the presence of apamin (control=6.5±0.64, n=4; mock=6.8±0.98, n=6; si16-treated=1.9±0.22, n=8; apamin and si16-treated=4.5±0.42, n=6). FIG. 4C is a summary plot of the maximum number at different current injections from si16-treated, and mock neurons. Data are mean±SEM.

FIG. 5A is a series of confocal dual channel images of dendritic segments of cultured hippocampal neurons. Scale bars=5 µm. FIG. 5B contains a schematic cartoon cross section of a dendrite, used in the postacquisition line scan analysis to quantify the distribution of $BK_{Ca}$ channel puncta. In this schematic, the distribution of cytoskeletal proteins MAP2 and $BK_{Ca}$ channel are represented as light gray core and dark gray dots respectively. For the line scan analysis, a region of interest, denoted by line perpendicular to the dendrite through a single z-section (dotted line on cartoon), was used to determine the distribution of $BK_{Ca}$ channel puncta (red arrows) along this point of reference in comparison to the MAP2 signal (green arrows). In the upper graph, $BK_{Ca}$ channels (dark gray line) are distributed inside and outside the diameter of MAP2 signal (light gray line). In the lower graph, $BK_{Ca}$ channels show a differential distribution that is more restricted to the diameter of MAP2 signal. FIG. 5C is a graph of the width of the signal as a function of control or si16-treated cultures (2.34±0.10; 2.03±0.12 µm, n=45 and 31 respectively).

FIG. 6A is a series of confocal images of a triple-channel image of dendritic segments of cultured hippocampal neurons. The left panels show the merged image of $BK_{Ca}$ channel and MAP2 and outlined-AlexaFluor 488 phalloidin (middle panels). The line scan profile (left panel) represents $BK_{Ca}$ channel fluorescence intensity between black arrowheads point (in middle panel). The grey dotted line in right panel demarcates the edge of phalloidin staining which corresponds to the morphology of spines. Scale bars=5 µm. The righthand panels are graphs of the fluorescence intensity as a function of width of lumen of dendritic spines in untreated versus si16-treated neurons. FIG. 6B is a graph of phalloidin and $BK_{Ca}$ fluorescence intensities between untreated and i16-specific siRNA-treated neurons. FIG. 6C is a graph depicting the correlation of dendritic spine and $BK_{Ca}$ channel localization with si16 treatment. 88.33% (41.67%-si16 treated culture; n=60, p<0.001) of control spine head contain more than 50% $BK_{Ca}$ channel signal as compared to fluorescence intensity of phalloidin. Data are mean±SEM.

FIG. 8 is a graph depicting the tissue distribution of $BK_{Ca}$ channel intron-containing transcripts that contain exon 17a.

FIG. 9 is a graph depicting the tissue distribution of exon 17b-containing $BK_{Ca}$ channel intron-containing transcripts that also contain exon 17a.

DETAILED DESCRIPTION OF THE INVENTION

Definitions

Figure 1A:
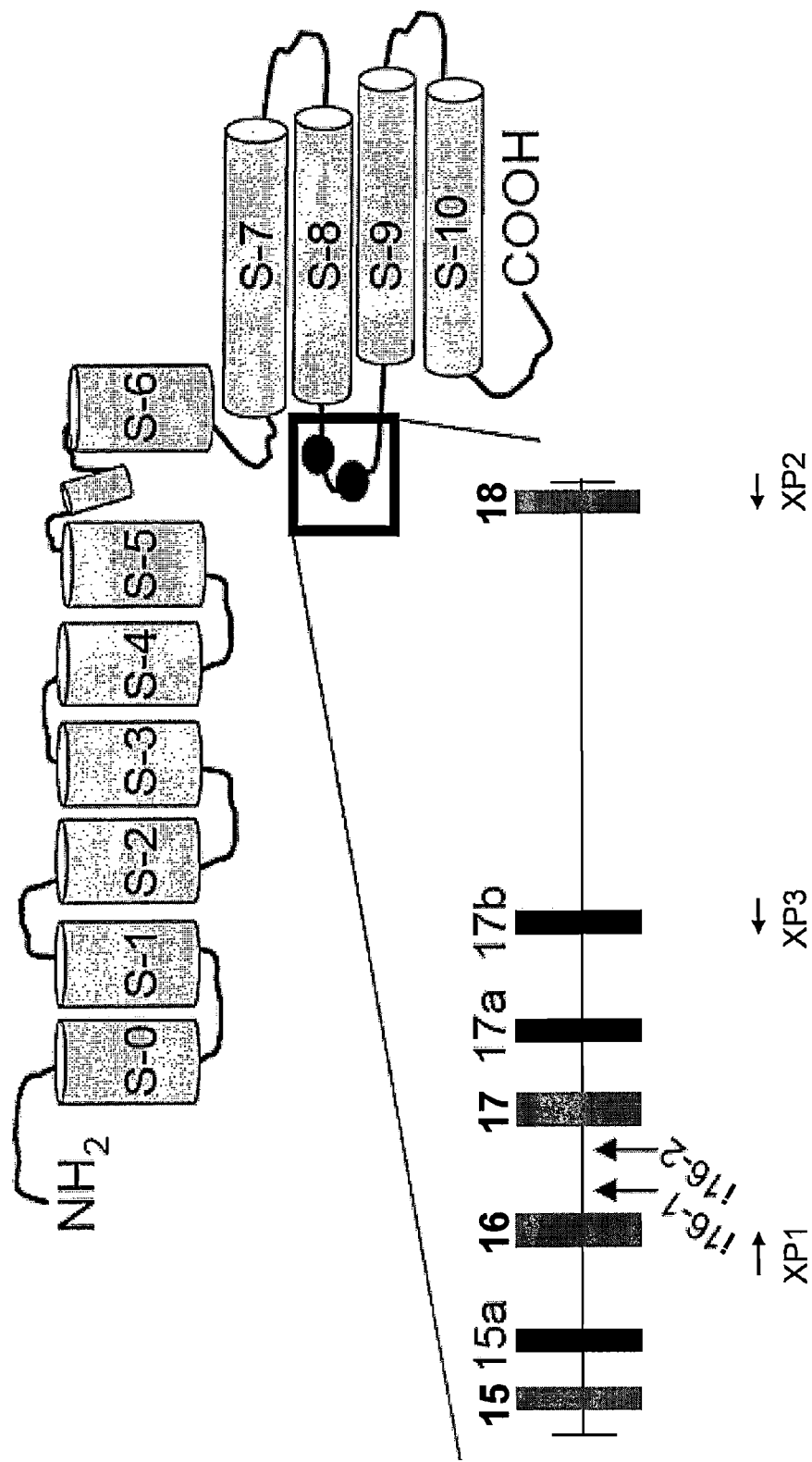

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and nucleic acid chemistry and hybridization are those well known and commonly employed in the art.

Standard techniques are used for nucleic acid and peptide synthesis. The techniques and procedures are generally performed according to conventional methods in the art and various general references (e.g., Sambrook and Russell, 2001, Molecular Cloning, A Laboratory Approach, Cold Spring Harbor Press, Cold Spring Harbor, N.Y., and Ausubel et al., 2002, Current Protocols in Molecular Biology, John Wiley & Sons, NY), which are provided throughout this document.

The nomenclature used herein and the laboratory procedures used in analytical chemistry and organic syntheses described below are those well known and commonly employed in the art. Standard techniques or modifications thereof, are used for chemical syntheses and chemical analyses.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

As used herein, to "alleviate" a disease, disorder or condition means reducing the severity of one or more symptoms of the disease, disorder or condition.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

In the context of the present invention, the following abbreviations for the commonly occurring nucleic acid bases are used. "A" refers to adenosine, "C" refers to cytidine, "G" refers to guanosine, "T" refers to thymidine, and "U" refers to uridine.

A "polynucleotide" means a single strand or parallel and anti-parallel strands of a nucleic acid. Thus, a polynucleotide may be either a single-stranded or a double-stranded nucleic acid.

The term "nucleic acid" typically refers to large polynucleotides.

The term "oligonucleotide" typically refers to short polynucleotides, generally, no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

A "portion" of a polynucleotide means at least at least about twenty sequential nucleotide residues of the polynucleotide. It is understood that a portion of a polynucleotide may include every nucleotide residue of the polynucleotide.

As used herein, to "treat" means reducing the frequency with which symptoms of a disease, disorder, or adverse condition, and the like, are experienced by a patient.

As the term is used herein, "modulation" of a biological process refers to the alteration of the normal course of the biological process. The term "modulating the cytoplasmic level of an intron-containing mRNA" as used herein refers to either increasing or decreasing the level of the intron-containing mRNA compared to the level of intron-containing mRNA in the absence of the modulation.

As used herein, "function of a neuron" refers to any naturally-occurring activity exhibited in neuron. Such activities include membrane depolarization, action potential, excitability, spike activity including frequency and/or number of spikes, activity of specific ion channels, synaptic formation and synapse function.

As used herein "siRNA" refers to small interfering RNAs, which are involved in the phenomenon of RNA interference (RNAi). siRNAs are typically about 21 to about 25 nucleotides long, are double-stranded and 100% homologous to a portion of a coding sequence. However, as used herein, the term "siRNA" encompasses all forms of siRNA including, but not limited to (i) a double stranded RNA polynucleotide, (ii) a single stranded polynucleotide, and (iii) a polynucleotide of either (i) or (ii) wherein such a polynucleotide, has one, two, three, four or more nucleotide alterations or substitutions therein. If an siRNA is single stranded, its sequence is homologous to a portion of the antisense strand of a coding sequence.

"Homologous" as used herein, refers to nucleotide sequence similarity between two regions of the same nucleic acid strand or between regions of two different nucleic acid strands. When a nucleotide residue position in both regions is occupied by the same nucleotide residue, then the regions are homologous at that position. A first region is homologous to a second region if at least one nucleotide residue position of each region is occupied by the same residue. Homology between two regions is expressed in terms of the proportion of nucleotide residue positions of the two regions that are occupied by the same nucleotide residue. By way of example, a region having the nucleotide sequence 5'-ATTGCC-3' and a region having the nucleotide sequence 5'-TATGGC-3' share 50% homology. Preferably, the first region comprises a first portion and the second region comprises a second portion, whereby, at least about 50%, and preferably at least about 75%, at least about 90%, or at least about 95% of the nucleotide residue positions of each of the portions are occupied by the same nucleotide residue. More preferably, all nucleotide residue positions of each of the portions are occupied by the same nucleotide residue.

As used herein, "otherwise identical neuron" refers to a neuron from the same species of organism and same type of neuronal tissue that another neuron is from, and subjected to the same conditions, such as culture conditions, as the other neuron. Preferably, the otherwise identical neuron comes from the same neuronal tissue source as the other neuron.

As used herein, a "neural network" refers to an interconnected network of neurons, and may include other components.

It is understood that any and all whole or partial integers between any ranges set forth herein are included herein.

DESCRIPTION

The instant invention springs in part from the discovery of intron-containing mRNAs in the somatodendritic cytoplasm of neurons. Under normal cellular conditions, unspliced or incompletely spliced intron-containing mRNAs are routinely sequestered within the nucleus (Dreyfuss et al., 2002, Nat Rev Mol Cell Biol 3: 195-205; Rutz et al., 2000, EMBO J. 19: 1873-1886) and, when transported to the cytoplasm, are subject to cellular nonsense-mediated degradation (Hillman et al., 2004, Genome Biol 5: R8; Lejeune et al., 2005, Curr Opin Cell Biol 17: 309-315). Intron retention has been described for cyclooxygenase 3 (Cui et al., 2004, Neurochemical Research 29: 1731-1737; Shaftel et al., 2003, Brain Research 119: 213-215) and sodium channel β1a variants (Kazen-Gillespie et al., 2000, The Journal of Biological Chemistry 275: 1079-1088). However, these events are rarely observed in higher eukaryotes (Galante et al., 2004, RNA 10: 757-765). In fact, database entries annotating intron-containing mRNAs often represent them as artifacts with little likelihood of influencing cellular physiology. Recently, however, several reports have begun to pinpoint a mechanism for promoting the nuclear export of incompletely spliced intron-containing mRNAs (Denis et al., 2005, Cell 122: 379-391; Li et al., 2006, Nature 443: 234-237).

Specifically, the invention relates to the discovery that intron-containing mRNAs for the pore-forming α-subunit of $BK_a$ channel, KCNMA1, for amyloid beta A4 precursor protein (AMB4), for potassium channel Kv4.2 (Kv4.2), and for microtubule-associated protein-2 (MAP2) are present in somatodendritic cytoplasm. It is believed that the identification of these several different intron-containing mRNAs in the somatodendritic cytoplasm suggests that the localization of intron-containing mRNAs in the neuronal cytoplasm may be a generalized phenomenon. Furthermore, intron-containing $BK_{Ca}$ channel transcripts were also observed in cells of other tissue types. Specifically, transcripts with either 16-1 or 16-2 intronic regions were also detected in heart cells, testis cells, skeletal muscle cells, fetal brain cells and fetal testis cells. These data suggest that the localization of intron-containing mRNAs, including splice variants comprising introns, in specific subcellular locations may be a general phenomenon. The discovery described herein suggests that intron-containing mRNAs are biologically relevant, which contradicts suggestions in the prior art that such intron-containing mRNA are merely artefactual. Accordingly, identification and characterization of intron-containing mRNAs is contemplated as a basis for identifying novel therapeutic targets for diseases and disorders.

In addition, it has been unexpectedly discovered the $BK_{Ca}$ channel intron-containing mRNA contributes to the intrinsic membrane properties of hippocampal neurons. Specifically, the $BK_{Ca}$ channel intron-containing mRNA functionally contribute to the intrinsic firing properties of hippocampal neurons. The intron 16 (i16)-containing mRNAs are $Ca^2$-regulated. A bath-applied depolarizing stimulus is sufficient to distinctly alter the abundance and distribution of the i16-containing mRNA. Notable, the localization patterns of spliced $BK_{Ca}$ channel mRNAs expressing backbone exons 22-25 (e22-25) are unaffected by these modulators of synaptic activity. Furthermore, as shown herein for the $BK_{Ca}$ channel i16-containing mRNA, the exported transcript does not merely collect in the area adjacent to the nucleus, but rather, it forms a somatodendritic pool that is highest in concentration at the most proximal portions of the dendrites and diminishes with distance from the cell body. This pattern of localization is notable in that it mimics the gradient in $BK_{Ca}$ channel functional activity (Poolos et al., 1999, J Neurosci 19: 5205-5212). As demonstrated herein, it has been further discovered that $BK_{Ca}$ channel i16-containing mRNAs are essentially all found in one splice variant; specifically, all of the i16-containing transcripts skip exon 17a and exon 17b and splice exon 17 directly to exon 18. Thus, $BK_{Ca}$ channel i16-containing mRNAs exclude exons 17a and 17b.

Accordingly, the invention provides a method of modulating the function of a neuron by modulating the cytoplasmic level of an intron-containing mRNA in the neuron. The methods of the instant invention have myriad useful applications. In general, the methods and compositions of the present invention are useful in neurobiological research including neurodegenerative disease research, drug development for neurodegenerative diseases and diagnostic and therapeutic methods for neurodegenerative diseases.

In one embodiment, the method involves decreasing the level of cytoplasmic intron-containing KCNMA1 mRNA, thereby decreasing the excitability of the neuron. The method of decreasing the level of intron-containing KCNMA1 mRNA has therapeutic application to alleviate or treat disorders, diseases or conditions characterized by undesirable or excessive neuronal excitability. Exemplary diseases include epilepsy and chronic obstructive pulmonary disease. It is contemplated that detecting an altered level of intron-containing KCNMA1 mRNA in somatodendritic cytoplasm compared to the level in a normal neuron is useful for the diagnosis of such disease.

MAP2 and AMB4 are affected in the etiology of Alzheimer's disease. Kv4.2, a subunit of A-type $K^+$ channels, is thought to play a critical role in modulation of neuronal excitability and nociceptive behaviors and thus play a role in pain plasticity. Thus, the methods of the invention may be useful in the diagnosis and/or treatment of disorders and diseases associated with these proteins. The invention further provides methods of diagnosis of a disease or disorder, such as a neurodegenerative disease, based on detection of an altered amount of cytoplasmic intron-containing mRNA as compared to the level in a healthy but otherwise identical neuron. Methods of therapy to alleviate and/or treat neurodegenerative diseases, based on increasing or decreasing the cytoplasmic level in a neuron of an intron-containing mRNA, are also contemplated in the invention. Neurodegenerative diseases, diseases and conditions include, but are not limited to, Parkinson's disease, Alzheimer's disease, Huntington's disease, amyotrophic lateral sclerosis, Fragile X syndrome, Downs' syndrome, and neuropsychiatric illnesses, such as depression, schizophrenia, and schizo-affective disorders.

The methods of the instant invention can be practiced using any neuron or dendrite of a neuron. Preferred neurons are those of mammals, including both non-human mammals as well as humans. Particularly preferred neurons in the practice of the instant invention are those of rats, mice and humans. The methods of the instant invention may be practiced using an isolated neuron, or a neuron in a neural network. An isolated neuron can be maintained in culture, including primary cell culture and slice culture. Furthermore, the methods of the invention may be practiced using a neuron that is in vivo, in a living organism. The neuron can also be a transplanted neuron, either in vitro in culture or in vivo in an animal. The neuron may also be a transplanted neuron that is not a part of a neural network, but has the potential to be stimulated to integrate into an existing neural network.

The instant invention includes methods of modulating the excitability of a neuron by modulating the cytoplasmic level of intron-containing mRNA in a neuron. As shown in the examples presented herein, decreasing the level of intron-containing KCNMA1 mRNA decreases excitability of the neuron. Decreasing the level of intron-containing mRNA can be accomplished using any method known to the skilled artisan. Examples of methods to decrease the level of intron-containing mRNA include, but are not limited to, increasing the rate of splicing of the intron-containing mRNA and decreasing expression of an intron-containing mRNA.

In one preferred embodiment, the cytoplasmic level of intron-containing mRNA is decreased by administering an activator of splicing of the intron-containing mRNA. As used herein, an "an activator of splicing" is any compound that increases the splicing of the intron-containing mRNA. Preferably, the activator is specific for splicing of the intron-containing mRNA.

In another embodiment, expression of an intron-containing mRNA is decreased. Methods of decreasing expression of an intron-containing mRNA include, but are not limited to, methods that use siRNA, antisense, ribozymes and other specific inhibitors of intron-containing mRNA expression.

In another preferred embodiment, siRNA is used to decrease the level of an intron-containing mRNA. RNA interference (RNAi) is a phenomenon in which the introduction of double-stranded RNA (dsRNA) into a diverse range of organisms and cell types causes degradation of the complementary mRNA. In the cell, long dsRNAs are cleaved into short 21-25 nucleotide small interfering RNAs, or siRNAs, by a ribonuclease known as Dicer. The siRNAs subsequently assemble with protein components into an RNA-induced silencing complex (RISC), unwinding in the process. Activated RISC then binds to complementary transcript by base pairing interactions between the siRNA antisense strand and the mRNA. The bound mRNA is cleaved and sequence specific degradation of mRNA results in gene silencing. See, for example, U.S. Pat. No. 6,506,559; Fire et al., 1998, Nature 391(19): 306-311; Timmons et al., 1998, Nature 395:854; Montgomery et al., 1998, TIG 14(7):255-258; David R. Engelke, Ed., RNA Interference (RNAi) Nuts & Bolts of RNAi Technology, DNA Press, Eagleville, Pa. (2003); and Gregory J. Hannon, Ed., RNAi A Guide to Gene Silencing, Cold Spring Harbor Laboratory Press, Cold Spring Harbor, N.Y. (2003). Soutschek et al. (2004, Nature 432:173-178) describe a chemical modification to siRNAs that aids in intravenous systemic delivery. Optimizing siRNAs involves consideration of overall G/C content, C/T content at the termini, Tm and the nucleotide content of the 3' overhang. See, for instance, Schwartz et al., 2003, Cell, 115:199-208 and Khvorova et al., 2003, Cell 115:209-216. Therefore, the present invention also includes methods of decreasing levels of an intron-containing mRNA using RNAi technology.

Similarly, increasing the cytoplasmic level of intron-containing mRNA in the methods of the invention can be accomplished using methods known to the skilled artisan. In one embodiment, the method of modulating the cytoplasmic level of intron-containing mRNA protein in a neuron includes increasing the level of intron-containing mRNA in a neuron by administering an inhibitor of splicing of the intron-containing mRNA. As used herein, an "an inhibitor of splicing" is any compound that inhibits or precludes splicing of the intron-containing mRNA. Preferably, the inhibitor is specific for splicing of the intron-containing mRNA.

Other methods for increasing the cytoplasmic level of an intron-containing mRNA include, but are not limited to, providing exogenous intron-containing mRNA to a neuron and expressing a recombinant polynucleotide sequence encoding an intron-containing mRNA. As will be understood by the skilled artisan, intron-containing mRNA useful in the present invention is prepared in any number of ways, and the method of preparation of RNA should not be considered to limit the invention in any way. By way of a non-limiting example, RNA useful in the present invention may be prepared by methods including isolation of native intron-containing mRNA from a neuron, isolation of intron-containing mRNA from a recombinant system in which a recombinant DNA construct is used to transcribe RNA, or from a recombinant RNA virus (e.g., rhinovirus, hepatitis C), modified to contain a coding sequence for the intron-containing mRNA. The RNA is introduced into a neuron by any method known in the art. In one embodiment, it is introduced by photoporation of the neuron. Other methods include lipid-mediated introduction of RNA into the neuron.

As will be understood by the skilled artisan, introducing an expression vector encoding an intron-containing mRNA into a neuron can be accomplished in any number of ways, and the method of introducing an expression vector should not be considered as limiting the invention in any way. Expression vectors and methods for the introduction of exogenous DNA into cells with concomitant expression of the exogenous DNA in the cells are described, for example, in Sambrook et al. (2001, Molecular Cloning: A Laboratory Manual, Cold Spring Harbor Laboratory Press, Cold Spring Harbor, N.Y.), and in Ausubel et al. (eds, 1997, Current Protocols in Molecular Biology, John Wiley & Sons, New York, N.Y.). Any expression vector compatible with the expression of RNA in neurons is suitable for use in the instant invention, and can be selected from the group consisting of a plasmid DNA, a viral vector, and a mammalian vector. The expression vector, or a vector that is co-introduced with the expression vector, can further comprise a marker gene. Marker genes are useful, for instance, to monitor transfection efficiencies. Marker genes include: genes for selectable markers, including but not limited to, G418, hygromycin, and methotrexate, and genes for detectable markers, including, but not limited to, luciferase and GFP. The expression vector can further comprise an integration signal sequence which facilitates integration of the isolated polynucleotide into the genome of a neuronal cell.

Inhibitors and activators of splicing of an intron-containing mRNA can be identified by screening test compounds, using conventional methods known to the skilled artisan. Test compounds for use in such screening methods can be small molecules, nucleic acids, peptides, peptidomimetics and other drugs. The test compounds of the present invention can be obtained using any of the numerous approaches in combinatorial library methods known in the art, including biological libraries, spatially-addressable parallel solid phase or solution phase libraries, synthetic library methods requiring deconvolution, the "one-bead one-compound" library method, and synthetic library methods using affinity chromatography selection. The biological library approach is limited to peptide libraries, while the other four approaches are applicable to peptide, nonpeptide oligomer, or small molecule libraries of compounds (Lam, 1997, Anticancer Drug Des. 12:145). Inhibitors and activators of splicing of an intron-containing mRNA may be useful in therapeutic applications, or serve as lead drugs in the development of therapeutics.

The instant invention includes methods of modulating the function of a cell by modulating the cytoplasmic level of an intron-containing mRNA in the cell. The cell may be from any tissue type. In an embodiment, the cell is from a tissue selected from the group consisting of heart, testis, brain and skeletal muscle. Any tissue may be of fetal origin. Modulating the cytoplasmic level may be accomplished by any method described elsewhere herein.

Treatment, Alleviation and Diagnosis of Disease

Reduction of the cytoplasmic level of intron-containing KCNMA1 mRNA or decreases neuron excitability. The present invention therefore provides a method for the treatment of a neurodegenerative disease whose pathology involves excitability in an individual, accomplished by decreasing the cytoplasmic level of intron-containing KCNMA1 mRNA. Methods of decreasing the cytoplasmic level of intron-containing KCNMA1 mRNA described elsewhere herein are applicable in the treatment method.

Kv4.2 is a subunit of A-type $K^+$ channels and plays a role in regulating action potential backpropagation and the induction of specific forms of synaptic plasticity (Chen et al., 2006, J Neurosci 26:12143-12151. Kv4.2 has also been shown to be critical site for modulation of neuronal excitability and nociceptive behaviors and thus may play a role in pain plasticity (Hu et al., 2006, Neuron 50:89-100). Accordingly, modulating the cytoplasmic level of intron-containing Kv4.2 mRNA is contemplated to be useful as a therapeutic method for neurodegenerative diseases whose pathology involves excitability, as diseases, disorder or conditions featuring nociceptive pain.

MAP2 plays a role in stabilizing microtubules in neurons, in dendrite elongation and in neurite initiation. It is also inappropriately sequestered in Alzheimers. AMB4 is known to play a critical role in the etiology of Alzheimer's. Accordingly, modulating the cytoplasmic level of intron-containing AMB4 or MAP2 mRNA is contemplated to be useful as a therapeutic method for Alzheimer's disease and other neurodegenerative diseases whose pathology involves impaired microtubule stabilization, dendrite elongation or neurite initiation.

In preferred embodiments, modulation of the cytoplasmic level of an intron-containing mRNA in a neuron is accomplished by administering siRNA or an activator or inhibitor of splicing.

The therapeutic methods of the invention thus encompass the use of pharmaceutical compositions of an appropriate small molecule, protein or peptide and/or isolated nucleic acid to practice the methods of the invention. The pharmaceutical compositions useful for practicing the invention may be administered to deliver a dose of between 1 ng/kg/day and 100 mg/kg/day. In one embodiment, the invention envisions administration of a dose which results in a concentration of the compound of the present invention between 1 $\mu$M and 10 $\mu$M in a mammal.

As used herein, the term "physiologically acceptable" ester or salt means an ester or salt form of the active ingredient which is compatible with any other ingredients of the pharmaceutical composition, which is not deleterious to the subject to which the composition is to be administered.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the description of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as non-human primates, cattle, pigs, horses, sheep, cats, and dogs.

Pharmaceutical compositions that are useful in the methods of the invention may be prepared, packaged, or sold in formulations suitable for oral, rectal, vaginal, parenteral, topical, pulmonary, intranasal, buccal, ophthalmic, or another route of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents.

Controlled- or sustained-release formulations of a pharmaceutical composition of the invention may be made using conventional technology.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Remington's Pharmaceutical Sciences (1985, Genaro, ed., Mack Publishing Co., Easton, Pa.), which is incorporated herein by reference.

The invention also contemplates assessing the cytoplasmic level of an intron-containing mRNA as the basis of diagnostic applications. The cytoplasmic level of an intron-containing mRNA can be assessed in a test neuron and in a healthy but otherwise identical neuron using any method known in the art, including but not limited to, immunoassays, hybridization assays, such as Northern blots, nuclease protection assays, in situ hybridization, gene array analysis and RT-PCR assays. Exemplary immunoassays include immunohistochemistry assays, immunocytochemistry assays, ELISA, capture ELISA, sandwich assays, enzyme immunoassay, radioimmunoassay, fluorescent immunoassay, and the like, all of which are known to those of skill in the art. See e.g. Harlow et al., 1988, Antibodies: A Laboratory Manual, Cold Spring Harbor Laboratory Press, Cold Spring Harbor, N.Y.; Harlow et al., 1999, Using Antibodies: A Laboratory Manual, Cold Spring Harbor Laboratory Press, Cold Spring Harbor, N.Y.

Novel Therapeutic Targets

As disclosed herein, an intron-containing mRNA localized in the cytoplasm has been discovered to play a role in the biological function of the neuronal cell. It is therefore contemplated that other intron-containing splice variants that are specifically localized subcellularly outside of the nucleus exist and are functionally relevant. Since inappropriate biological function typically underlies diseases and disorders, intron-containing mRNAs localized outside of the nucleus represent novel therapeutic targets. Thus, the invention encompasses methods of identifying splice variants comprising introns and characterizing their tissue and subcellular distribution, and their use as therapeutic targets. Further, the invention encompasses a method of screening test compounds for candidate therapeutic molecules that modulate the biological function of an extranuclear intron-containing mRNA. Such modulation includes, but is not limited to, modulating the translation of the mRNA and modulating the subcellular localization of the mRNA. The skilled artisan is familiar with the design of screening methods. Test compounds for use in such screening methods are described elsewhere herein.

EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

The materials and methods used in the following Experimental Examples are now described.

Hippocampal Cultures:

Primary cultures of hippocampal neurons from E19 rat embryos were plated on glass coverslips at 100,000 per ml in Neuralbasal media with B27 supplements (Sigma). Hippocampal neurons were dissociated in L-15 media with collagenase (20 mg/ml, Sigma) and dispase (96 mg/ml, Sigma). Enzymatic digestion was carried out at 37° C. for ~45 min and cells triturated periodically with a fire polished pipette to facilitate dissociation. Neurons were washed twice in 1×PBS (Gibco) and plated on poly-D-lysine (Sigma) coated covers slips in Neurobasal media (Gibco). Neurons were maintained at 37° C. with 5% $CO_2$ and used 10 to 14 days after isolation.

Dendrite RT-PCR analysis:

The pools of dendrites were harvested by negative pressure into glass micropipettes. Immediately upon the completion of collection the RNA from each sample was subjected to two rounds of aRNA amplification procedure using T7 RNA polymerase (Eberwine et al., 1992). cDNA was synthesized from amplified aRNA from dendrites samples using Superscript III (Invitrogen) and used as a template for PCR with the Advantage2 PCR system (BD Biosciences). One round of PCR was performed using a Robocycler® (Stratagene). For all sets of primers, the PCR reaction conditions were 1 cycle of 94° C. for 3 minute; 30 or 35 cycles of 94° C. for 1 minute, 59° C. for 1.5 minute, 72° C. for 1.5 minute, and a final cycle of 7 minute extension at 72° C. The PCR products were run on 2% agarose gels pre-stained with ethidium bromide. The PCR products were subcloned and sequenced to confirm their identity. Negative controls lacking cDNA were performed and processed in parallel PCR reactions.

PCR primers for 16-1 (330 basepairs; bp) were: 16-1 up (SEQ ID NO. 1) 5' cagacaggtgaggctaatgagggagacgagtaat;

16-1-dw (SEQ ID NO. 2) 5' aggatgggagttgttttggagtgagaa-gatgagc. Primers for 16-2 (390 bp) were: 16-2-up (SEQ ID NO. 3) 5' atctgcagacggaaatgtttgttgtaa; 16-2-dw (SEQ ID NO. 4) 5' tgtagtccctccttccctccagt. Primers for KCNMA1 (201 bp) were: KCNMA1-up (SEQ ID NO. 5) 5' gtttgcgaaactaaagctct-taatgatagcc; KCNMA1-dw (SEQ ID NO. 6) 5'cttttgggatctgt-gatgtcatcatgg.

Microarray Analysis:

Custom microarrays representing intronic regions of genes with reported dendritic localization were designed to include spotted PCR products from up to three introns from each gene of interest. Intronic sequences on these arrays represent partial sequences of a group of selected introns within the coding region. PCR products were generated using AccuPrime™ Supermix II (Invitrogen) with rat genomic DNA template isolated from rat liver hepatocytes. PCR reactions were carried out for 35 cycles using an annealing temperature of 55° C. generating specific products ranging from 400-500 by in size for each intronic region. Target sequences were amplified using this method representing regions of amyloid beta (A4) precursor protein introns 1, 6 and 17; potassium channel Kv4.2 introns 1, 2 and 4; microtubule-associated protein 2 introns 3, 4 and 12; and calcium/calmodulin-dependent protein kinase II alpha introns 1, 3 and 10. Primers for each of these target sequences are shown in Table 1.

used with equal success. Primary rat hippocampal cultures (10 to 14 days) were fixed for 15 minutes in 4% paraformaldehyde at room temperature, washed in 1×PBS and permeabilized with 1×PBS and 0.3% TritonX-100. Cells were pre-hybridized at 42° C. for ~4 hours with 50% formamide, 1×Denhardt's solution, 4×SSC, 10 mM DTT, 0.1% CHAPS, 0.1% Tween-20, 500 µg/µl yeast tRNA and 500 u µg/µl salmon sperm DNA. Hybridization was performed at 42° C. for ~16 hours with 15 ng/ul probe in prehybridization buffer with the addition of 8% Dextran sulfate. Anti-digoxigenin Fab fragments conjugated to Qdot 565 were used for detection. The samples were subjected to photobleaching to remove background autofluorescence before Qdot signal detection under an Olympus Fluoview 1000 confocal scan head attached on inverted microscope. After photobleaching, images were captured with 458 nm excitation laser, and emissions were collected by spectral detector range of 550-594 nm spectrum. All the images were captured with same parameters. The metamorph image processing program were used to process images with same settings otherwise noted on the figure legend. For these ISH, two procedures were used: one procedure was based upon alkaline phosphatase and nitroblue tetrazolium (NBT)/5'-bromo-4-chloro-3'-indolyphosphate (BCIP) detection and a second procedure was based upon fluorescent Qdot detection of RNAs. The first procedure

TABLE 1

| Protein | Intron # | Primer direction | SEQ ID NO. | Sequence |
|---|---|---|---|---|
| Amyloid beta (A4) protein | Intron 1 | Forward primer | 7 | 5'-tggccgcctggacggttc-3' |
|  |  | Reverse primer | 8 | 5'-tgagacactgcgctttcg-3' |
|  | Intron 6 | Forward primer | 9 | 5'-ccactgagtctgtggagg-3' |
|  |  | Reverse primer | 10 | 5'-ccagcccagtgaatgacc-3' |
|  | Intron 17 | Forward primer | 11 | 5'-tacacatccatccatcat-3' |
|  |  | Reverse primer | 12 | 5'-cagggcccaaacaaaaca-3' |
| Kv4.2 | Intron 1 | Forward primer | 13 | 5'-gtacaccatcgtcaccat-3' |
|  |  | Reverse primer | 14 | 5'-ggcaaacctagacttccaaaca-3' |
|  | Intron 2 | Forward primer | 15 | 5'-caacgagcggacaaacga-3' |
|  |  | Reverse primer | 16 | 5'-gcccgatttctaagggataaa-3' |
|  | Intron 4 | Forward primer | 17 | 5'-cacctgcttcactgcctg-3' |
|  |  | Reverse primer | 18 | 5'-cccatccctcctttgctt-3' |
| Microtubule-associated protein 2 | Intron 3 | Forward primer | 19 | 5'-acaaggatcagcctgcag-3' |
|  |  | Reverse primer | 20 | 5'-tgggaaatggcaaggcta-3' |
|  | Intron 4 | Forward primer | 21 | 5'-catcagaacaaacagctg-3' |
|  |  | Reverse primer | 22 | 5'-agggctgggggaagttct-3' |
|  | Intron 12 | Forward primer | 23 | 5'-caccatgtacctggaggt-3' |
|  |  | Reverse primer | 24 | 5'-ccctccttcccgtttgag-3' |
| Calcium/calmodulin-dependent protein kinase II alpha | Intron 1 | Forward primer | 25 | 5'-agagtaccagctcttcga-3' |
|  |  | Reverse primer | 26 | 5'-gcgggggtgaagtctctc-3' |
|  | Intron 3 | Forward primer | 27 | 5'-gaggggcaccactacctt-3' |
|  |  | Reverse primer | 28 | 5'-tcccatgtgctcctgtcc-3' |
|  | Intron 10 | Forward primer | 29 | 5'-tggactttcatcgattct-3' |
|  |  | Reverse primer | 30 | 5'-actgggcatctgggatga-3' |

100 picogram (pg) of individual intronic PCR products were spotted over a diameter of 150 microns on glass slides. Probe sequences for hybridization to these arrays were generated from approximately 150 mechanically-isolated dendrites from primary rat hippocampal neurons cultured for 13 days. Dendritic mRNA was amplified using two rounds of aRNA amplification and single stranded, Cy3-labeled cDNA probes were used to screen the array.

In Situ Hybridization Using Cultured Hippocampal Neurons:

Antisense digoxigenin-labeled KCNMA1 RNA probes (350 to 550 bp) were generated by in vitro transcription. wo separate non-overlapping probes against i16 transcripts were is utilized in FIG. 3 to provide a good detail of cellular morphology in comparison to the mRNA signal detected with alkaline phosphatase and NBT and BCIP. Conventional protocols for fluorescent ISH did not yield a reproducibly consistent signal for the low-abundance $BK_{Ca}$ channel variant mRNA ISH. A pre-imaging photobleaching process eliminates endogenous autofluorescence and, in combination with the robust stability and lack of photobleaching of Qdots, permits low level signal to be detected. This procedure was used to generate the data in FIGS. 1e and 2.

In Situ Hybridization Using Adult Rat Brain Sections:

Antisense digoxigenin-labeled KCNMA1 RNA probes (350 to 550 bp) were generated by in vitro transcription. Fresh frozen adult rat brains were sectioned at 15 μm thickness. The brain sections were fixed for 15 minutes in 4% paraformaldehyde at room temperature, washed in 1×PBS and permeabilized with 1×PBS and 0.3% TritonX-100. Sections were prehybridized at 42° C. for ~4 hours with 50% formamide, 1×Denhardt's solution, 4×SSC, 10 mM DTT, 0.1% CHAPS, 0.1% Tween-20, 500 μg/μl yeast tRNA and 500 μg/μl salmon sperm DNA. Hybridization was performed at 42° C. for ~16 hours with 2 ng/μprobe in prehybridization buffer with the addition of 8% Dextran sulfate. Anti-digoxigenin Fab Fragments conjugated to alkaline phosphatase (Roche) were used for detection and were subjected to NBT/BCIP (Roche) staining for visualization under brightfield optics with a Zeiss Axiovert microscope.

Antibodies:

The primary antibodies used were a polyclonal $BK_{Ca}$ channel (Alomone Labs) at 1:150 and monoclonal MAP2 (a gift of V. Lee) at 1:250. The secondary antibodies used were anti-rabbit Alexa 546 and anti-mouse Alexa 488 at 1:400 (Molecular Probes). Anti-digoxigenin Fab Fragments conjugated to Qdot 565 (Invitrogen) or alkaline phosphatase (Roche) were used at 1:250. AlexaFluor 488 phalloidin (Molecular Probes) was used according to the manufactures protocol at 1:40.

Immunocytochemistry:

Primary rat hippocampal neurons were fixed on glass coverslips 10-14 days after plating, permeabilized with 0.3% TritonX-100, and processed for staining. Neurons were blocked at room temperature for 60 minutes in 3% bovine serum albumin, 1×PBS and 0.1% Tween-20. The primary and secondary antibodies were diluted in the blocking solution. The neurons were washed with 1×PBS with 0.1% Tween-20. Images were visualized with a FluoView™ 1000 confocal scan head (Olympus Corporation). For each cell, five randomly placed line scans were taken from three separate regions of interest for each dendritic segment and analyzed with Metamorph® image processing software.

Confocal Imaging and Data Analysis:

ISH samples were subjected to photobleaching to remove background autofluorescence before Qdot signal detection under an Olympus Fluoview 1000 confocal scan head. After photobleaching, images were captured with 458 nm excitation laser and emissions were collected by spectral detector range of 550-594 nm spectrum. All the images were captured with same parameters. The Metamorph image processing program was used to process images with same settings.

Line scan analysis for $BK_{Ca}$ channel protein distribution was performed after image acquisition. From whole cell images, region of interest were selected based on MAP2 staining, and a random 1×25 pixel line scan area perpendicular to MAP2 orientation was used to obtain intensity profiles for MAP2 and $BK_{Ca}$ channel signal. These data are presented as fluorescence intensity as a function of distance from the center of the MAP2 signal.

For spine head analysis (FIG. 6), a 25 pixel round region of interest was randomly assigned in the phalloidin image channel, and fluorescence intensities from other channels was measured. Statistical test was performed by Sigmaplot program. At least 2 different batches of cell culture were used for each experiment.

Pharmacological Treatments:

Hippocampal neurons were maintained at 37° C. with 5% $CO_2$ and used within 10 to 14 days after isolation. The culture were treated and returned to 37° C. with 5% $CO_2$ for six hours. Membrane depolarization was induced by 25 mM KCl treatments. Three classes of voltage-gated calcium channels blockers were added to the cultures for 1 minute prior to depolarization: for Cav2.1 (P/Q-type) 1 μM ω-conotoxin MVIIC (Calbiochem); for Cav2.2 (Ntype) 1 μM ω-conotoxin GVIA (Calbiochem); and for Cav1.3 (L-type) 1 μM nifedipine (Calbiochem). After treatment, the cultures were fixed for 15 minutes in 4% paraformaldehyde at room temperature, washed in 1×PBS and stored at 4° C. until utilized for ISH analysis.

siRNA Treatments:

Cultured primary rat hippocampal neurons were transfected according to the Dharmafect (Dharmacon) protocol 7-9 days after plating with 20 nM siRNA-Glo Rhodamine marker (Dharmacon) or with 2 sets of siRNAs each directed against a different sequence of the KCNMA1 intron 16 (300 nM total) or a non-KCNMA1 target sequence (Ambion negative control nos. 1 and 7) and 20 nM siRNA-Glo Rhodamine marker. The transfection solution was removed 24 hr after and replaced with 50% conditioned and 50% fresh Neuralbasal media. The cultures were maintained at 37° C. with 5% $CO_2$ for 72 hours and used for ISH, immunocytochemistry, or electrophysiology analyses. The i16-specific siRNAs were synthesized at University of Pennsylvania Nucleic Acid Facility. siRNAs for i16 were: 16-1A antisense (SEQ ID NO. 31) 5' cugagcuucuggagaagaguu; siRNA 16-1A sense (SEQ ID NO. 32) 5' cacuucuccagaagcucaguu; siRNA 16-1B antisense (SEQ ID NO. 33) 5' cggagguggugguaagaguuuu; and siRNA 16-1B sense (SEQ ID NO. 34) 5' aacucuuacaccagguccguu.

Whole Cell Recordings:

Hippocampal neurons were placed into the recording chamber containing bathing solution consisting of 140 mM NaCl, 3 mM KCl, 1 mM $CaCl_2$, 1 mM $MgCl_2$, 10 mM HEPES, adjusted to a pH of 7.4 with NaOH. Viable, transfected neurons were visually identified by siRNA-Glo Rhodamine marker (Dharmacon). Patch electrodes had a resistance of 2-4 M. The internal solution consisted of 120 mM potassium gluconate, 20 mM KCl, 10 mM HEPES, 0.1 mM EGTA, 2 mM $MgCl_2$, 2 mM ATP, 0.25 mM GTP adjusted to a pH of 7.4 with KOH. Seals were formed in bathing solution and whole cell configuration was obtained by negative pressure. A current-clamp protocol from a holding potential of −80 mV with 500 millisecond test pulses of different amplitudes was then randomly delivered. Data acquisition was performed using HEKA EPC10 (HEKA Instruments). IGOR software was used for data analysis. All recordings were obtained at room temperature.

MALDI-TOF MS and Quantitative KCNMA1 Splice Variant Detection:

Initial PCR samples were amplified in 5 ml of 100 nM $MgCl_2$ at 2.75 mM, and 200 mM dNTP using 0.1 units of HotStart TaqDNA polymerase (Qiagen) with the following PCR conditions: 95° C. hot start for 15 minutes, followed by 45 cycles of 95° C. for 30 seconds, 56° C. for 1 minute, then 72° C. for 3:30 minutes, with a final hold of 72° C. of 7 minutes. After the PCR amplification, the products were treated with 0.04 units of shrimp alkaline phosphatase, SAP (Sequenom), which inactivates unused dNTPs from the amplification cycles, for 25 minutes at 37° C. followed by heat inactivation at 85° C. for 5 minutes. For the extension cycle, 1.2 mM final concentration of extension primer and 0.6 units of ThermoSequenase (Sequenom) were added to a total reaction of 9 ml with the termination mix containing specific dideoxynucleotides and deoxynucleotides for each reaction at 50 mM for each base. The extension conditions include a 94° C. hold for 2 minutes with 99 cycles of the following: 94° C. for 5 seconds, 52° C. for 5 seconds, and 72° C. for 7 seconds. The primers for KCNMA1 analysis were as follows: forward (e16), 5' taattaaccctgggaaccac (SEQ ID NO. 35); i16 forward, 5' tcctgaagaatgcccacttg (SEQ ID NO. 36); All reverse (e18), 5' atgtgttgggtgagttcctc (SEQ ID NO. 37); XP1, 5' tagcctcacctgtctga (SEQ ID NO. 38); XP2, 5' cggttgctcatct-tcaa (SEQ ID NO. 39); and XP3, 5' tgtagatggacatcttgg (SEQ ID NO. 40).

Matrix-assisted laser desorption/ionization time-of-flight mass spectrometry (MALDI-TOF MS) base extension was used to determine the levels and endogenous populations of i16-containing transcripts. In this method, cDNA is amplified with two sets of primers: exon 16 (e16) forward and exon 18 (e18) reverse to capture "all transcripts" or i16-1 forward and e18 reverse to capture "only i16-containing transcripts." The extension reaction uses extension primers that bind directly across the splice junction. Therefore, multiple distinct extension primers can assess several splicing junctions on the same transcript allowing the relative relationship of each splicing event to be interconnected. Next, these unique extension products representing the different splicing transcripts are quantified via MALDI-TOF MS. This method was chosen over real-time PCR because of its higher sensitivity to low abundance transcripts (Yang et al., 2005, PNAS 102: 7683-7688). Three different extension primers were used. XP1 is located on the 3' end of e16 and was used to identify either e16-e17 or i16-e17 transcripts.

To analyze the endogenous exonic combination between i16 to e18, two different extension primers were used. This region consists of four downstream exons: two constitutive exons (e17 and e18) and two alternatively spliced exons (e17a and e17b). Therefore, this region of the KCNMA1 transcript has the potential to generate four distinct exonic combinations or variants: e17-e18, e17-e17a-e18, e17-e17b-e18, or e17-e17a-e17b-e18. The XP2 extension primer was placed at the 5' end of e18 and was used to identify the presence of e17, e17a, e17b on the upstream side of e18. The XP3 extension was placed at the 5' side of e17b, and was used to identify transcripts presence or absence e17a on the upstream side of e17b.

Before MALDI-TOF MS analysis, salts from the reactions were removed using SpectroCLEAN resin and 16 ml of water. ASV analysis was performed using the MassARRAY system (Sequenom) by dispensing ~10 nl of final product onto a 384-plate format MALDI-TOF MS SpectroCHIP using a SpectroPOINT nanodispenser (Sequenom). The frequency of each variant was generated by SpectroTYPER (Sequenom) and was determined by taking the ratio normal variant area. Additionally, the data quality was controlled by discarding data with a frequency error (a weighted uncertainty of the frequencies for each variant) greater than 10.0%. Level of quantification (LOQ) for the MALDI-TOF platform has been previously reported using pooled allele frequency as 5.0% (Ross et al., 2000, BioTechniques 29:620-626, 628-629). A peak was considered detected if it had a signal-to-noise ratio greater than ten. After the data were filtered for quality, the mean and standard deviation for each splice variant was calculated as the final reported value.

The results of the experiments are now described.

Experimental Example 1

$BK_{Ca}$ Channel Intron-Containing mRNAs are Present in Hippocampal Dendrites

Figure 1B:
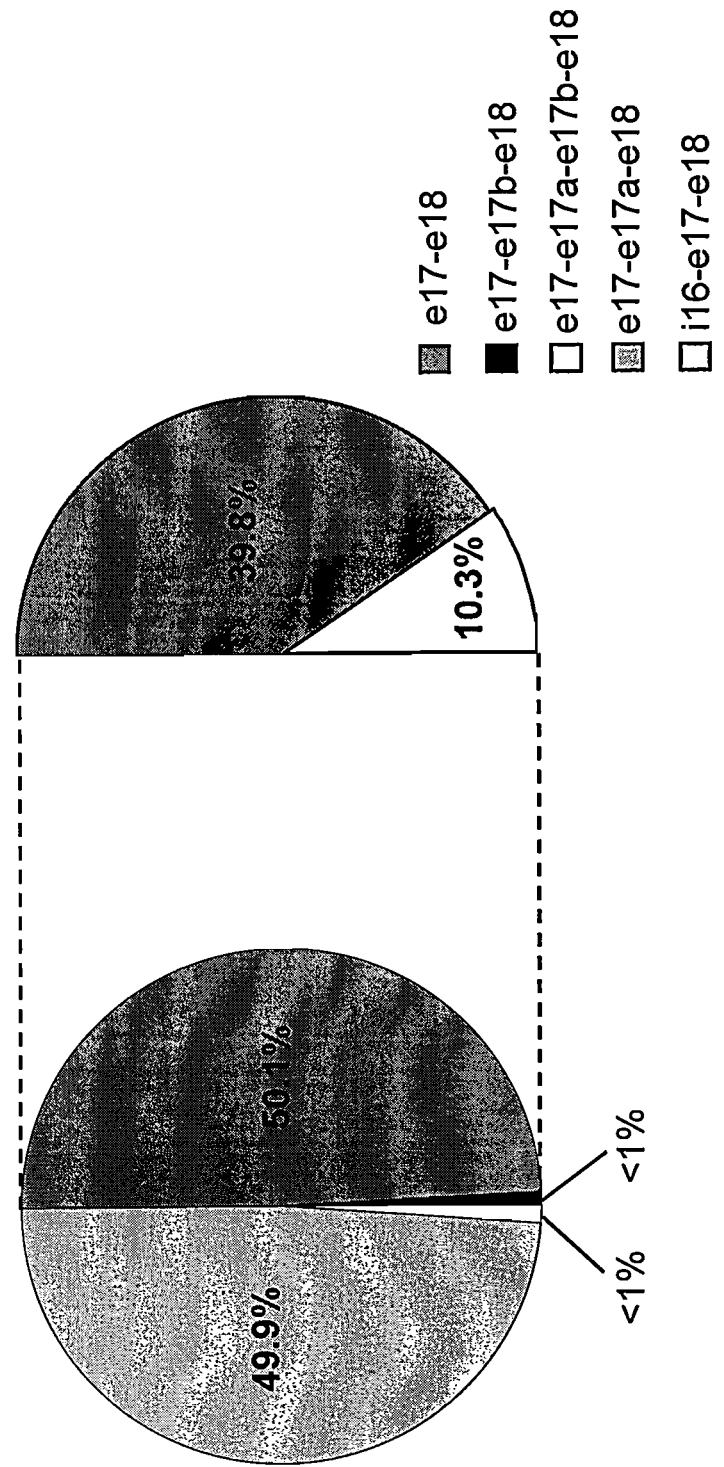
Figures 1C, 1D, 1E:
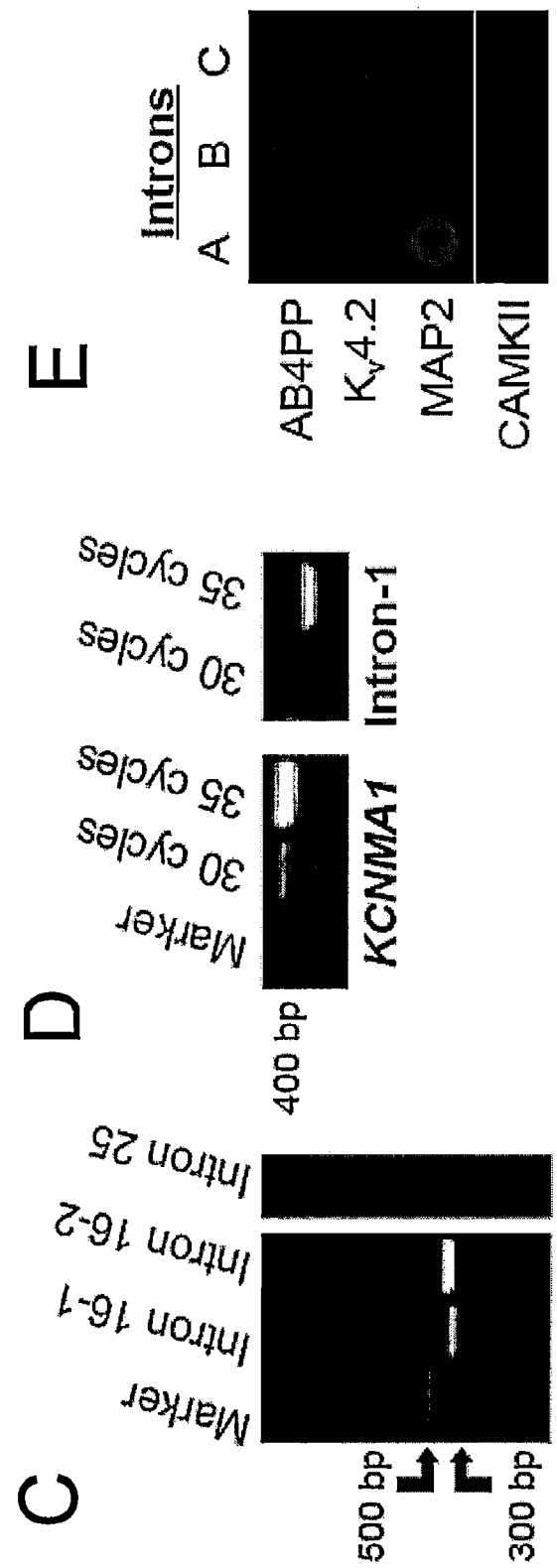

To determine the repertoire of mRNA variants in the postsynaptic compartment, a cDNA template, derived from aRNA amplification of poly-A mRNA isolated from rat hippocampal dendrites harvested 14-21 days in vitro (Crino et al., 1996, Neuron 17: 1173-1187; Miyashiro et al., 1994, Proceedings of the National Academy of Sciences of the United States of America 91: 10800-10804), was prepared. Dendrites were carefully harvested individually to insure that no cell bodies, and thus nuclei, of any neuron or non-neuronal cell were harvested. From this starting material, unexpectedly, two separate polymerase chain reaction (PCR) products were detected using primers specific to intron 16 of KCNMA1 (FIG. 1C). Intron 16 (i16) is approximately 6000 nucleotides in length, and is upstream of a previously described "hotspot" for alternative exon usage (Chen et al., 2005, The Journal of Biological Chemistry 280: 33599-33609). Exons surrounding i16 encode the 3'-end of the first of two highly-conserved $Ca^{2+}$-binding RCK (regulators of conductance $K^+$ channel) domains and the nonconserved linker region spanning the first and second RCK module (Jiang et al., 2002, Nature 417: 515-522; Quirk et al., 2001, Neuron 32: 13-23) (see FIG. 1A). The nucleotide sequence of the PCR products (330 and 390 nucleotides) proved to be identical to the rat genomic $BK_{Ca}$ channel genomic DNA sequence deposited in GenBank® as Accession number NW_043710. Intron 25 (i25) sequence could not be amplified (FIG. 1C) showing that the selective amplification of i16-containing sequence is not due to genomic contamination. Previously, studies have demonstrated that KCNMA1 splice variants represent a small subset of the total KCNMA1 transcript population (MacDonald et al., 2006, BMC Developmental Biology 6: 37). Here RT-PCR experiments demonstrate that the backbone KCNMA1 exon PCR, spanning exons 22 to 25 (KCNMA1e22-e25), was more readily detectable than i16-containing $BK_{Ca}$ channel mRNA from dendrite samples as expected. Indeed, KCNMA1 and i16-containing $BK_{Ca}$ channel PCR products were robustly detected by RT-PCR at 30 and 35 cycles respectively (FIG. 1C). These data show that KCNMA1 is higher abundance than the i116-containing mRNA.

Microarray analysis was used to screen for the presence of other intron-containing mRNA fragments in amplified poly-A mRNA dendrite samples. The presence and absence of select introns from four dendritically-targeted genes was examined: amyloid beta precursor (AMB4), potassium channel Kv4.2 (Kv4.2), microtubule-associated protein-2 (MAP2) and calcium/calmodulin-dependent protein kinase II (CAMKII) (Eberwine et al., 2002; Johnston et al., 2000) (see FIG. 1E). The introns detected in dendritically-localized AMB4, Kv4.2 and MAP2 mRNAs were not restricted to any particular region of the gene (5' or 3' end), demonstrating that the dendrite samples contained a complex population of mRNA transcripts. Furthermore, the presence of multiple intron-containing mRNAs in the cytoplasm of hippoccampal dendrites indicates that intron retention of dendritic mRNAs is not restricted to the $BK_{Ca}$ channel gene. The absence of selected introns from each of these mRNAs, including the complete absence of any of the screened introns from CaMKII gene, confirms that genomic contamination was not present in the dendrite samples. Additionally, in situ hybridization (ISH) analyses confirmed the dendritic localization of the other intron-containing mRNAs presented in FIG. 1E.

The levels and endogenous populations of i16-containing transcripts were resolved by MALDI-TOF MS base extension (McCullough et al., 2005, Nucleic Acids Res. 33:e99). This PCR method uses an identical probe to analyze multiple transcripts. Therefore, it was chosen over real-time PCR, which requires different exon-spanning probes to identify alternative spliced transcripts. Using this approach, the levels of i16-containing transcripts was first determined. Hippocampal tissue cDNA was amplified with PCR primers in exon 16 (e16) forward and e18 reverse to capture the "all $BK_{Ca}$ channel transcripts" population. A single extension primer (XP1) was used to assay the PCR products. The i16-containing transcript represented 10.3%±2.3% of the total $BK_{Ca}$ channel transcript population (FIG. 1B). The levels of i16-containing transcripts reported here are in agreement with a previous study showing other KCNMA1 splice variants typically represent a small subset (~10%) of the total KCNMA1 transcript population (MacDonald et al., 2006, BMC Dev Biol. 6:37).

The endogenous KCNMA1 exonic combination between i16 to e18 in both hippocampal tissue and isolated dendrites was then determined. This region consists of four downstream exons: two constitutive exons (e17 and e18) and two alternatively spliced exons (e17a and e17b). cDNA was amplified with two sets of PCR primers: (i) e16 forward and e18 reverse to capture "all $BK_{Ca}$ channel transcripts" or (ii) i16-1 forward and e18 reverse to capture "only i16-containing transcripts" (FIG. 1B). The PCR products were simultaneously assayed with the two different extension primers (XP2 and XP3) to capture all four exonic combinations (FIG. 1B). In the "all $BK_{Ca}$ channel transcripts" population, every exonic combination was detected, but two highly abundant variants, e17e18 and e17e17a-e18, made up the bulk of the $BK_{Ca}$ channel transcript population (FIG. 1B). A remarkably different pattern of splicing was detected in the "only i16-containing transcript" population. Unexpectedly, only one splice variant was detected; all of the i16-containing transcripts skip e17a and e17b and splice e17 directly to e18 (FIG. 1B). These data show that i16-containing mRNAs are restricted to a subset of the KCNMA1 transcript population containing correctly spliced downstream exons, e17 and e18. Furthermore, these results highlight two key properties of i16-containing transcripts. First, they are present at biologically significant levels in the hippocampus, and, more surprisingly, the overall complexity of the i16-containing transcripts transcript population is less diverse then would be possible if all combinations of the downstream exons were associated with the retained intron.

Experimental Example 2

The Subcellular Localization of $BK_{Ca}$ Channel mRNAs and Intron-Containing mRNAs in Hippocampal Neurons A novel, highly-sensitive Quantum Dot-based ISH protocol was developed with i16-containing $BK_{Ca}$ channel mRNA-specific probes to visualize its endogenous subcellular localization throughout the somatodendritic compartment (FIG. 1F and U.S. provisional application 60/926,360, entitled "Low Light Fluorescence Detection at the Light Microscope Level," filed Apr. 25, 2007). This procedure allows detection of low abundance signals. For the i16-containing $BK_{Ca}$ channel mRNA, a series of puncta were detectable in the cell soma that extends into the proximal and distal dendrite. Signal intensity was strongest in the first 50 μm proximal segment of the dendrite and diminished as a function of distance from the cell soma. A comparison with the ISH signal of the KCNMA1 e22-25 exon probe of the mature $BK_{Ca}$ channel mRNA, showed a similar pattern of distribution (FIG. 1F). This pattern is coincident with where dendritic $BK_{Ca}$ channel activity is most concentrated, as observed in previous studies showing large conductance current predominating in the most proximal portions of the dendrite while decaying with distance from the cell body (Poolos et al., 1999, J Neurosci 19: 5205-5212). The importance of these data is twofold. First, they provide independent corroboration of the somatodendritic presence of the i16-containing $BK_{Ca}$ channel mRNA. Second, they represent, the first report of an endogenous intron-containing mRNA that is exported from the nucleus and transported to the somatodendritic cytoplasm. Furthermore, these phenomena are not restricted to cultured hippocampal neurons. By using ISH, the presence of i16-containing $BK_{Ca}$ channel mRNA in the proximal somatodendritic compartment of neurons in the hippocampus and striatum of adult rat brains was demonstrated (FIGS. 1G and 1H). Here, alkaline phosphatase and NBT/BCIP detection of the ISH signal was used for visualization under brightfield optics (rather than quantum dot fluorescence) to highlight the morphology of cells in the tissue sections.

Experimental Example 3

Calcium Signaling Regulation of i16-Containing $BK_{Ca}$ Channel mRNA

Figures 2A, 2B, 2C, 2D, 2E, 2F:
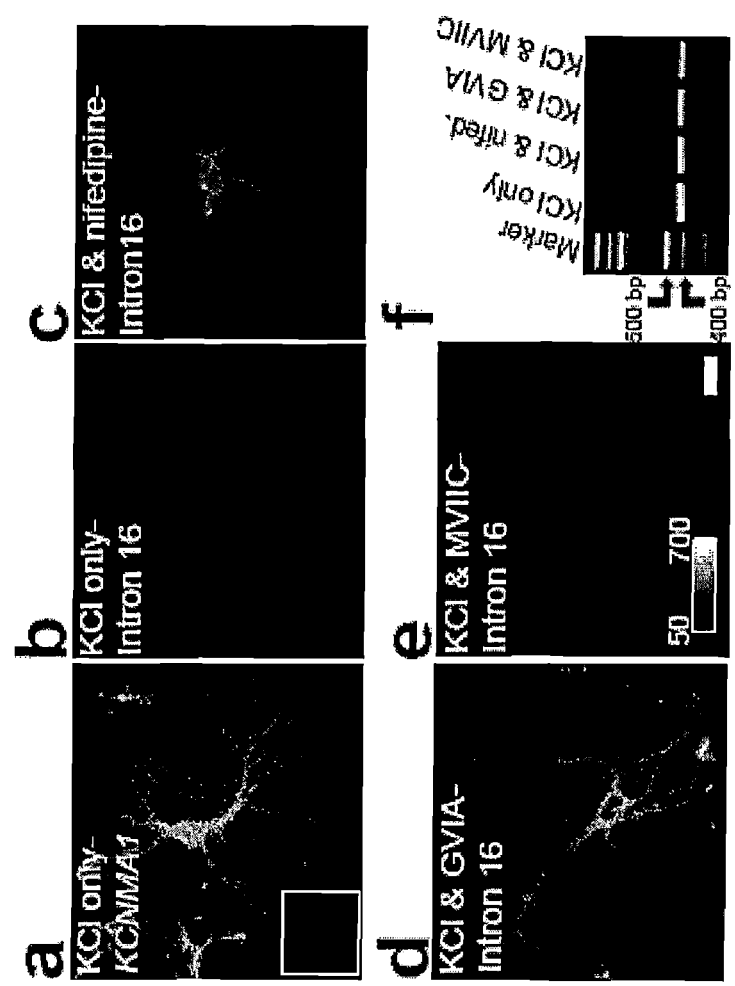
FIGS. 2A-2F are a series of images related to $Ca^{2+}$ signaling regulating i16-containing $BK_{Ca}$ channel mRNA levels in the somatodendritic compartment of hippocampal neurons. Cultured hippocampal neurons were exposed to KCl in the presence or absence of the indicated pharmacological drug treatments. The samples were fixed, and the expression patterns of i16-containing $BK_{Ca}$ channel mRNA were analyzed by ISH (n=4).

To examine whether modulators of synaptic activity regulate the differential distribution of the i16-containing mRNA, a depolarizing (25 mM) IC stimulus was bath-applied. Activity-dependent changes in alternative splice variant expression (Mu et al., 2003, Neuron 40: 581-594) and mRNA localization (Mayford et al., 1996, Proceedings of the National Academy of Sciences of the United States of America 93: 13250-13255; Steward et al., 2001, Annual Review of Neuroscience 24: 299-325; Steward et al., 2001, Proceedings of the National Academy of Sciences of the United States of America 98: 7062-7068; Tongiorgi et al., 1997, J Neurosci 17: 9492-9505) are key modulators of synaptic transmission and plasticity. Indeed, the depolarization-induced differences in the mRNA levels of one $BK_{Ca}$ channel splice variant, the stress-regulated exon (STREX) insert, are thought to contribute to differences in $Ca^{2+}$-sensitivity (Xie et al., 1998, Science 280: 443-446) and channel inhibition (Tian et al., 2004, Proceedings of the National Academy of Sciences of the United States of America 101: 11897-11902). The bulk of the mRNAs containing exons 22-25 of KCNMA1 were unresponsive to modulators of synaptic activity (FIG. 2, panel A). However, consistent with STREX isoform reports in neurons (Xie et al., 2005, RNA 11: 1825-1834), the levels of i16-containing $BK_{Ca}$ channel mRNA dramatically decreased in comparison to controls after depolarization (FIG. 2B). The Cav2.2 (N-type) and Cav1.3 (L-type) antagonists, co-conotoxin GVIA and nifedipine respectively, blocked the reduction in i16-containing mRNA levels and the normal distribution of puncta in the somatodendritic cytoplasm was maintained (FIGS. 2C and 2D). However, the Cav2.1 (P/Q-type) channel antagonist co-conotoxin MVIIC did not block the effects of depolarization upon i16-containing $BK_{Ca}$ channel mRNAs (FIG. 2E).

To confirm the observation that mature $BK_{Ca}$ channel mRNA is unaffected by such modulators of depolarization, PCR was performed. It was observed that $BK_{Ca}$ channel mRNAs expressing exons 22-25 were consistent over the various pharmocological treatments (FIG. 2F). These data indicate that the localization of mature $BK_{Ca}$ channels α-subunit mRNAs expressing constitutive backbone exons (e22-e25) was unchanged in the presence of any of the channel blockers tested (FIG. 2F).

It is unclear how this differential distribution of different $BK_{Ca}$ channel mRNAs occurs. These results, however, highlight the dynamic regulation of the localization and abundance of cytoplasmic i16-containing $BK_{Ca}$ channel mRNAs in response to $Ca^{2+}$-mediated modulators of synaptic activity.

Experimental Example 4

Figures 3A, 3B, 3C, 3D:
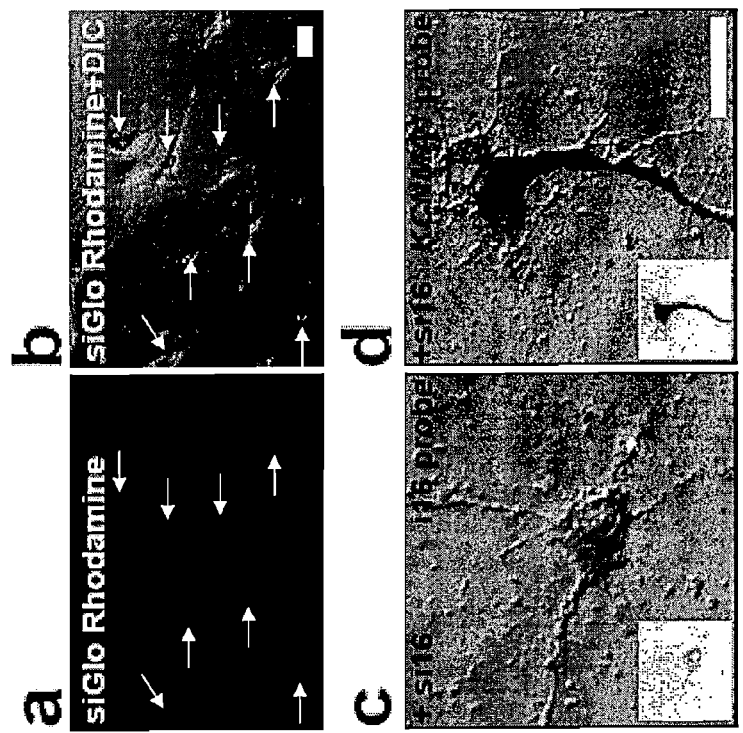
FIGS. 3A-3D are a series of images related to i16-specific siRNA treatment. Cultured primary rat hippocampal neurons were transfected 7-9 days after plating with 20 nM siGlo Rhodamine marker only (mock-treated) or with a pool of 2 distinct siRNAs directed against i16-containing (si16-treated) $BK_{Ca}$ channel mRNA (300 nM final concentration total) and 20 nM siGlo Rhodamine marker.

BK$_{Ca}$ Channel Intron-Containing mRNAs Contribute to the Excitability of Hippocampal Neurons To determine whether i16-containing BK$_{Ca}$ channel mRNAs contribute to hippocampal neuron firing patterns, a protocol to selectively reduce their expression levels was optimized. Two non-overlapping, short-interfering RNAs (siRNAs), specific for the i16 sequence (si16), were synthesized and transfected (individually and combined) into primary hippocampal neurons. The siRNA-treated hippocampal neurons maintained normal cellular morphology and were visually identified by the present of the siRNA Glo Rhodamine (FIGS. 3A and 3B). Using ISH, i16-specific siRNA treatment was observed to deplete the pools of i16-containing BK$_{Ca}$ channel mRNA in the cytoplasm of hippocampal neurons (FIG. 3C). As a control for off-target effects, each of the two non-overlapping i16-1 siRNAs were transfected individually yielding the same phenotype. In contrast, the mature BK$_{Ca}$ channels α-subunit mRNAs expressing backbone exons (e22-e25) were unchanged in abundance and subcellular distribution in si16-treated neurons as expected (FIG. 3D). ISH was also used with alkaline phosphatase and NBT/BCIP staining for detection and visualization under brightfield optics here to highlight the cellular morphology of the siRNA-treated neurons. siRNAs exert their function in the cytoplasm (Ohrt et al., 2006, Nucleic Acids Res 34: 1369-1380; Sen et al., 2005, Nature Cell Biology 7: 633-636; Zeng et al., 2002, RNA 8: 855-860). These siRNAs are specific for the cytoplasmically-localized i16-specific mRNAs, as confirmed by the observation that there was no change in the steady state levels of BK$_{Ca}$ channel mRNAs expressing e22-25.

Hippocampal cells typically fire a burst of action potentials characterized by spike accommodation in which subsequent action potentials broaden often leading to spike failure (Hille., 2001, 3rd edn (Sunderland, Mass., Sinauer)). In hippocampal neurons, BK$_{Ca}$ channels play a role in both action potential repolarization (Poolos et al., 1999, J Neurosci 19: 5205-5212), as well as spike broadening during repetitive firing (Shao et al., 1999, The Journal of Physiology 521(1): 135-146). Complex spike bursts of this sort are thought to underlie some adaptive processes during the acquisition of learning and memory (Thomas et al., 1998, J Neurosci 18: 7118-7126). Abnormally large BK$_{Ca}$ channel currents are the primary cause for changes in the patterns of complex spikes in some forms of epilepsy and dyskinesia (Du et al., 2005, Nat Genet. 37: 733-738).

Having established an effective siRNA treatment protocol to selectively reduce i16-containing BK$_{Ca}$ channel mRNA levels, whole cell recordings from hippocampal neurons were taken, and their firing patterns and action potential profiles were analyzed. Mock-treated, non-KCNMA1 siRNA-treated (Ambion negative controls) or i16-treated neurons were not detectably different from the control sample, in either the shape of the evoked actions potentials or maximum number of evoked action potentials (FIGS. 4A and 4B; control=6.5±0.64, n=4; mock=6.8±0.98, n=6). Mock-treated, non-KCNMA1 siRNA-treated (Ambion negative controls) or i16-treated neurons were also not detectably different from the control sample in action potential threshold, resting membrane potential or input resistance. However, the maximum number of evoked action potentials was significantly reduced in the si16-treated neurons (FIGS. 4A and 4B; si16-containing-treated=1.9±0.22, n=8), compared with control, mock-treated and non-KCNMA1 siRNA-treated neurons. These findings are consistent with a role for the i16-containing mRNA levels in the regulation of functional BK$_{Ca}$ channel expression and membrane excitability.

Experimental Example 5

Figures 4A, 4B, 4C:
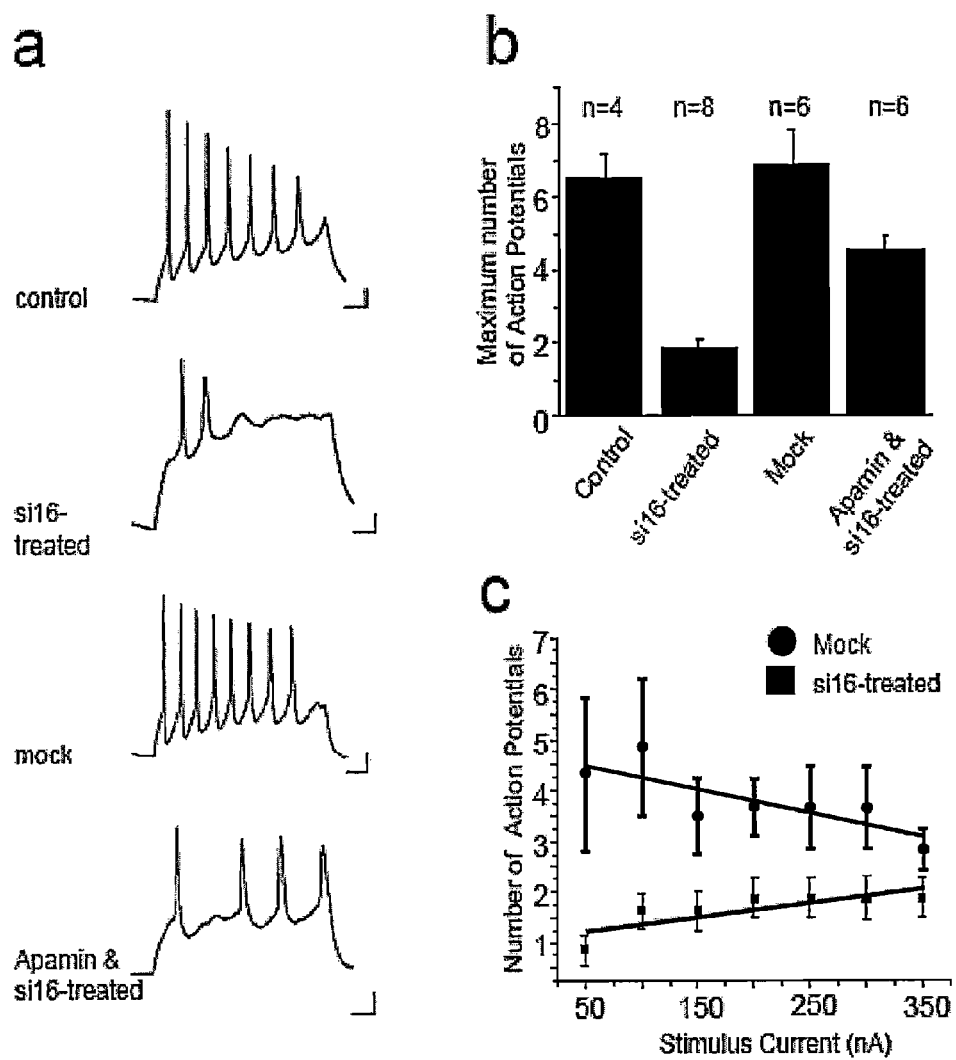
FIGS. 4A-4C are a series of traces and graphs relating to the firing properties of hippocampal neurons altered by i16-specific siRNAs. Hippocampal cultures neurons were cultured for approximately one week and subjected to the siRNA transfection protocol. After treatment, the neurons were cultured for an additional 72 hours and used for whole cell recordings. The neurons were current-clamped at −80 mV, and brief current injections (500 ms) were applied to evoke a train of action potential.

Spike Accommodation in Hippocampal Neurons Requires the Presence of BK$_{Ca}$ Channel Intron-Containing mRNAs To further characterize the functional significance of the i16-containing BK$_{Ca}$ channel mRNA, the input-output function of mock-treated and i16-specific siRNA-treated neurons was compared. With small current injections, the mock-treated neurons showed brisk spiking activity. However, as the size of the current injections increased, spike accommodation became more apparent and reduced the number of spikes fired (FIG. 4C). In contrast, the si16-treated cells exhibited marked spike accommodation even for small current injections, essentially leaving the neurons unable to encode different stimulus levels (FIG. 4C). These results demonstrate that a reduction in BK$_{Ca}$ channel α-subunit intron-containing mRNA levels alters membrane excitability of hippocampal neurons. These data are consistent with previous studies demonstrating that changes in BK$_{Ca}$ channel activity alter the membrane properties (Gu et al., 2007, J Physiol 580(Pt.3):859-82. Epub 2007 Feb. 15). Furthermore, these findings suggest cytoplasmic intron-containing mRNAs represent a novel form of gene expression regulation in hippocampal neurons.

Experimental Example 6

SK Channel Inhibition Increases the Excitability of i16-Specific siRNA-Treated Neurons Reduction of BK$_{Ca}$ channel intron-containing mRNA levels mimics the proposed role for the β4 subunit in the regulation of the KCNMA1α-subunit (Brenner et al., 2005, Nat Neurosci 8: 1752-1759) where the fast BK$_{Ca}$ channel is precluded by the β4 subunit from contributing to membrane depolarization. This allows for activation of the slower small-conductance Ca$^{2+}$-dependent K$^+$ (SK) channel and guards against hyperexcitability through more pronounced spike accommodation. One apamin-sensitive isoform, SK2, is localized throughout the postsynaptic compartment in both the shaft and spines of dendrites (Cai et al., 2004, Neuron 44: 351-364; Ngo-Anh et al., 2005, Nat Neurosci 8: 642-649). Thus, to test the notion that the reduction of i16-containing mRNA levels is reducing functional BK$_{Ca}$ channel activity and increasing SK channel activity, the firing patterns of i16-specific siRNA-treated neurons was analyzed in the presence of SK channel blocker apamin. The maximum number of evoked action potentials was observed to be significantly increased in si 16-treated neurons in the presence of apamin (FIG. 4B; apamin and si16-treated=4.5±0.42; n=6). Collectively, these results are consistent with previous studies which suggest that BK$_{Ca}$ channel activity is an intrinsic determinant of membrane properties. Moreover, they offer the first evidence for a functional role of a cytoplasmically-localized, endogenous intron-containing mRNA in altering the membrane excitability of hippocampal neurons.

Experimental Example 7

Figures 5A, 5B, 5C:
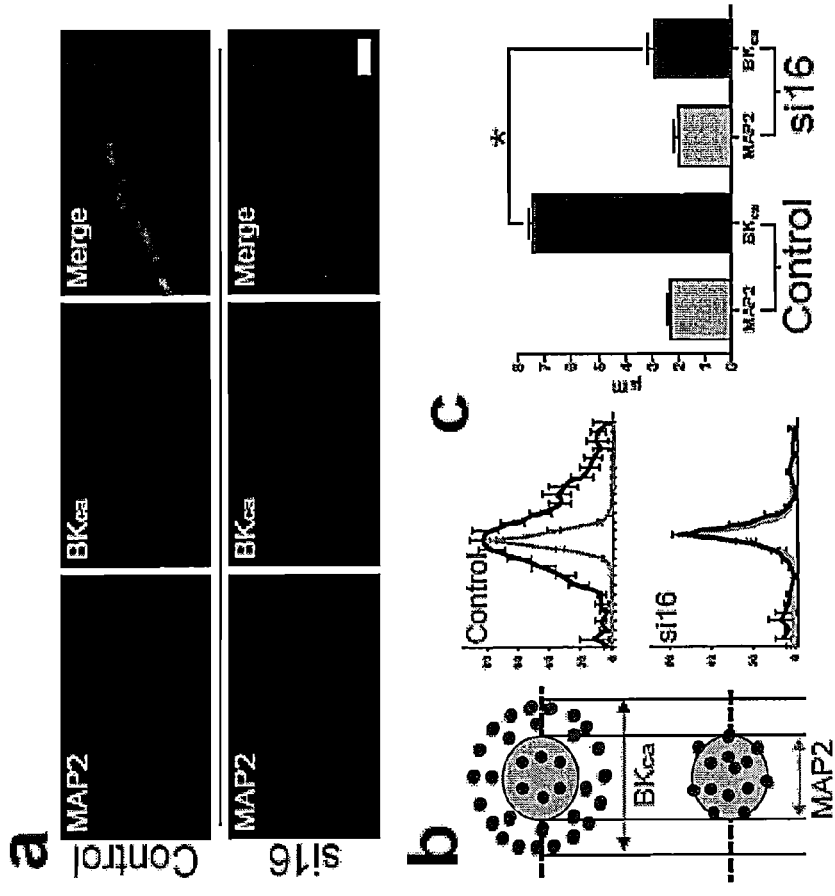
FIGS. 5A-5C are a series of images and graphs relating to the distribution pattern of $BK_{Ca}$ channel protein in hippocampal dendrites following i16-specific siRNA treatment.

Reducing BK$_{Ca}$ Channel i16-Containing mRNA Levels Alters the Distribution of BK$_{Ca}$ Channel Protein in Dendrites Given the altered firing properties upon the reduction of the cytoplasmic levels of i16-containing BK$_{Ca}$ channel mRNA, experiments were designed to assess the abundance and localization patterns of $BK_{Ca}$ channel protein in i16-specific siRNA-treated and untreated neurons using indirect immunofluorescence. While no large decrease in $BK_{Ca}$ channel protein was observed, there is a clear influence of i16-containing $BK_{Ca}$ channel mRNA on the subcellular distribution of $BK_{Ca}$ channel protein. Normally, a pattern of discrete puncta of $BK_{Ca}$ channel protein is distributed throughout the length of the somatodendritic compartment (Misonou et al., 2006, J Comp Neurol 496: 289-302). To quantify the distribution of $BK_{Ca}$ channel, line scan analysis (see schematic in FIG. 5B) performed through dendritic segments to determine how frequently puncta were colocalized with a primary structural protein in the dendrite, microtubule-associated protein 2 (MAP2). The signal observed from $BK_{Ca}$ channels or MAP2 at any one point along the line scan was reconstructed, and this data was presented in graphical format (FIG. 5B). Multiple line scans were performed in each dendritic segment of each cell. On average, $BK_{ca}$ channel puncta were dispersed in a wide arc with puncta positioned laterally and overlapping with the length of MAP2 signal (FIG. 5B). In si16-treated neurons, a nearly uniform colocalization of signals was observed. Statistical analysis of these data (Student's t test, $p<0.001$) demonstrated that there is no statistical difference in the width of MAP2 signal. In contrast, $BK_{Ca}$ channel signal shows more than twice the width in distribution of puncta in control (7.40±0.23 µm, n=45) compared to si16-treated (2.92±0.25 µm, n=31) cultures. The ~2-fold difference in the average width of the $BK_{Ca}$ channel distribution in mock-treated versus si 16-treated cultures underscores their divergence in differential distribution (FIG. 5C).

Experimental Example 8

Figures 6A, 6B, 6C:
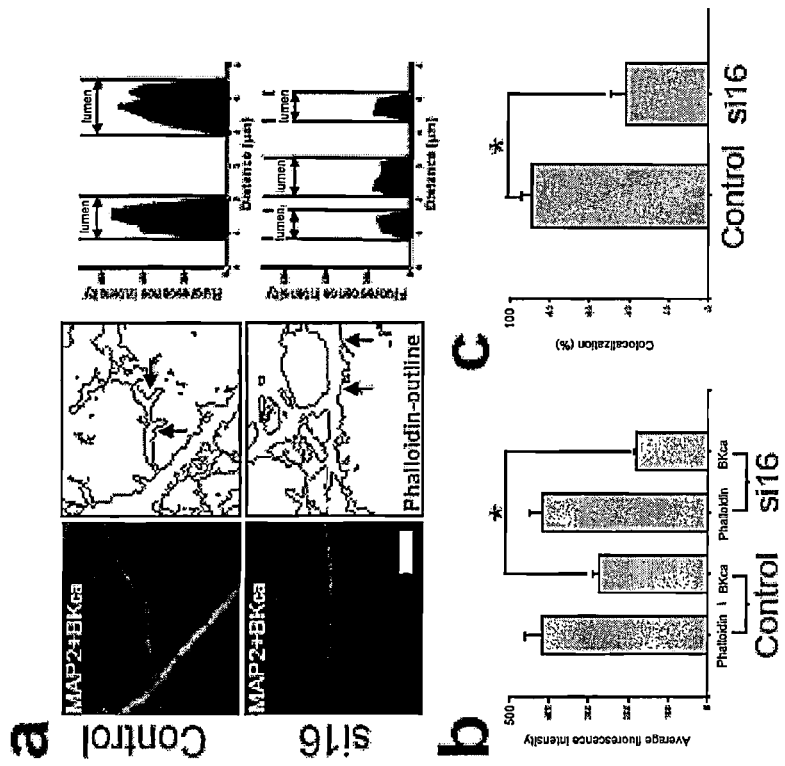
FIGS. 6A-6C are a series of images and graphs related to i16-specific siRNAs modification of the differential distribution of $BK_{Ca}$ channel protein in dendritic spines.

$BK_{Ca}$ Channel i16-Containing mRNAs Contribute Significantly to the Populations of $BK_{Ca}$ Channel in Dendritic Spines Given the striking change observed in the pattern of $BK_{Ca}$ channel distribution in the dendrite, the distribution of this channel in dendritic spines was assessed. This was accomplished by using triple label fluorescence. MAP2 staining was again used to identify dendritic processes in hippocampal neurons (FIG. 6A, lefthand images). Phallotoxins bind with high affinity to the filamentous actin (F-actin) and are frequently used to identify and quantify the levels of the cytoskeletal protein in tissue sections and cultured cells (Fischer et al., 1998, Neuron 20: 847-854; Halpain et al., 1998, J Neurosci 18: 9835-9844; Wang et al., 1982, Methods in Enzymology 85(B): 514-562). Dendritic spines and their filopodial precursors in hippocampal neurons contain a high abundance of F-actin. To quantify the distribution of $BK_{Ca}$ channels in dendritic spines, the frequency with which $BK_{Ca}$ channel puncta were observed to be colocalized with F-actin in spine-structures was determined using volume measurement analysis. The fluorescence intensity signal observed from $BK_{Ca}$ channels and phalloidin in dendritic spines of untreated and si 16-treated neurons was then compared (FIG. 6). One plane in a z-stack was taken to show the representative signal obtained with MAP2 and $BK_{Ca}$ channel antibodies. Outlined next to the photomicrograph is the boundary of Alexa 488-phalloidin staining within the same optical section (FIG. 6A, middle images). For the initial analysis, a line scan across dendritic spines (as represented between the two arrows) highlights the presence of $BK_{Ca}$ channel protein within the lumen of the spine. In si 16-treated neurons, a smaller but consistently-detectable $BK_{Ca}$ channel fluorescence intensity was noted in comparison to controls (FIG. 6a, righthand panel). These data are evidence of a differential distribution of $BK_{Ca}$ channels in the lumen of dendritic spines in untreated versus si 16-treated neurons.

Dendritic spines are dynamic structures with variable three-dimensional topography. It is possible that the line scan analysis may be biased if the pixels analyzed correspond to some spines that are only partially in the optical section, while others are being bisected directly in the middle of the spine lumen. To address this possibility, a region of interest was selected in multiple, randomly selected spine heads in the same optical section. Phalloidin fluorescence was analyzed first. Any difference in phalloidin signal would strongly imply that similar volumes of lumen within the spine head are not being compared. Importantly, there was no difference in the intensity of phalloidin staining between untreated and i16-specific siRNA-treated neurons (FIG. 6b, control; 419.09±43.01, n=60 and si16; 415.20±32.46, n=60). There was, in contrast, a quantifiable difference in $BK_{Ca}$ channel protein distribution (FIG. 6b, control; 274.47±14.97 and si16; 179.44±4.74, n=60, p<0.001).

To further refine this difference, the BK channel fluorescence intensity differences relative to phalloidin signal in FIG. 6b were transformed to reflect a measure of their incidence of colocalization. The observed BK channel fluorescence ranged from ~50 to 75% of the overall phalloidin signal in the spine heads of untreated neurons (FIG. 6c). Therefore, to be more rigorous the lower value (50%) was selected as the minimum parameter to establish the incidence of $BK_{Ca}$ channel and phalloidin colocalization. The spine heads showing equal 50% BK channel fluorescence intensity relative to phalloidin intensity were annotated as normal. Using these parameters of colocalization within a region of interest in a spine head, untreated cells were observed to be ±2 times more likely to have $BK_{Ca}$ channel protein in their spine heads above the 50% threshold, as compared to si16-treated cells (FIG. 6c). In untreated neurons, the $BK_{Ca}$ channel puncta predominately showed normal colocalization with phalloidin (~88%; FIG. 6c). A dramatic change in si16-treated neurons was observed in the colocalization pattern of $BK_{Ca}$ channel puncta in dendritic spines. Here, the colocalization incidence was significantly reduced (~42%; FIG. 6c). Collectively, these experiments highlight the local contribution i16-containing mRNAs make to the $BK_{Ca}$ channel protein distribution in hippocampal dendritic spines.

In parallel control experiments, the differential distribution of another member of the $K^+$ channel family, Kv2.1, was examined. As a prevalent component of the somatodendritic delayed-rectifier potassium currents in mammalian neurons, Kv2.1 plays a prominent role in regulating $Ca^{2+}$ influx and suppressing neuronal excitability (Misonou et al., 2004, Nat Neurosci 7:711-718). The colocalization of Kv2.1 channels with the phalloidin signature of individual dendritic spines was assessed. In contrast to the changes observed in $BK_{Ca}$ channel differential distribution, the localization of Kv2.1 was unaltered between control and si16-treated cultures (n=15; control, 85.0±7.2; si16, 83.3±8.0; Student's t test, P=0.88). As an additional control, the spine colocalization of the NR1 subunit of the NMDA receptor (Mu et al., 2003, Neuron 40:581-594) was assessed with and without i16 siRNA treatment. Again, no discernible difference was observed (n=13; control, 80.8±6.4, si16-treated, 75.0±9.4; Student's t test, P=0.66). These controls show that the siRNA-induced difference in $BK_{Ca}$ channel spine localization is selective.

Experimental Example 9

Tissue Distribution of Intron-Containing $BK_{Ca}$ Channel Transcripts and Various Exon Splice Forms To explore the prevalence of intron-containing BKCa channel transcripts, experiments were performed to assess the tissue distribution of such transcripts. Tissue distribution of particular exon splice forms were also assessed. Total RNA was extracted from the following tissues: heart, testis, skeletal muscle, fetal brain and fetal testis. Transcripts were detected by MALDI-TOF MS base extension.

Figure 7:
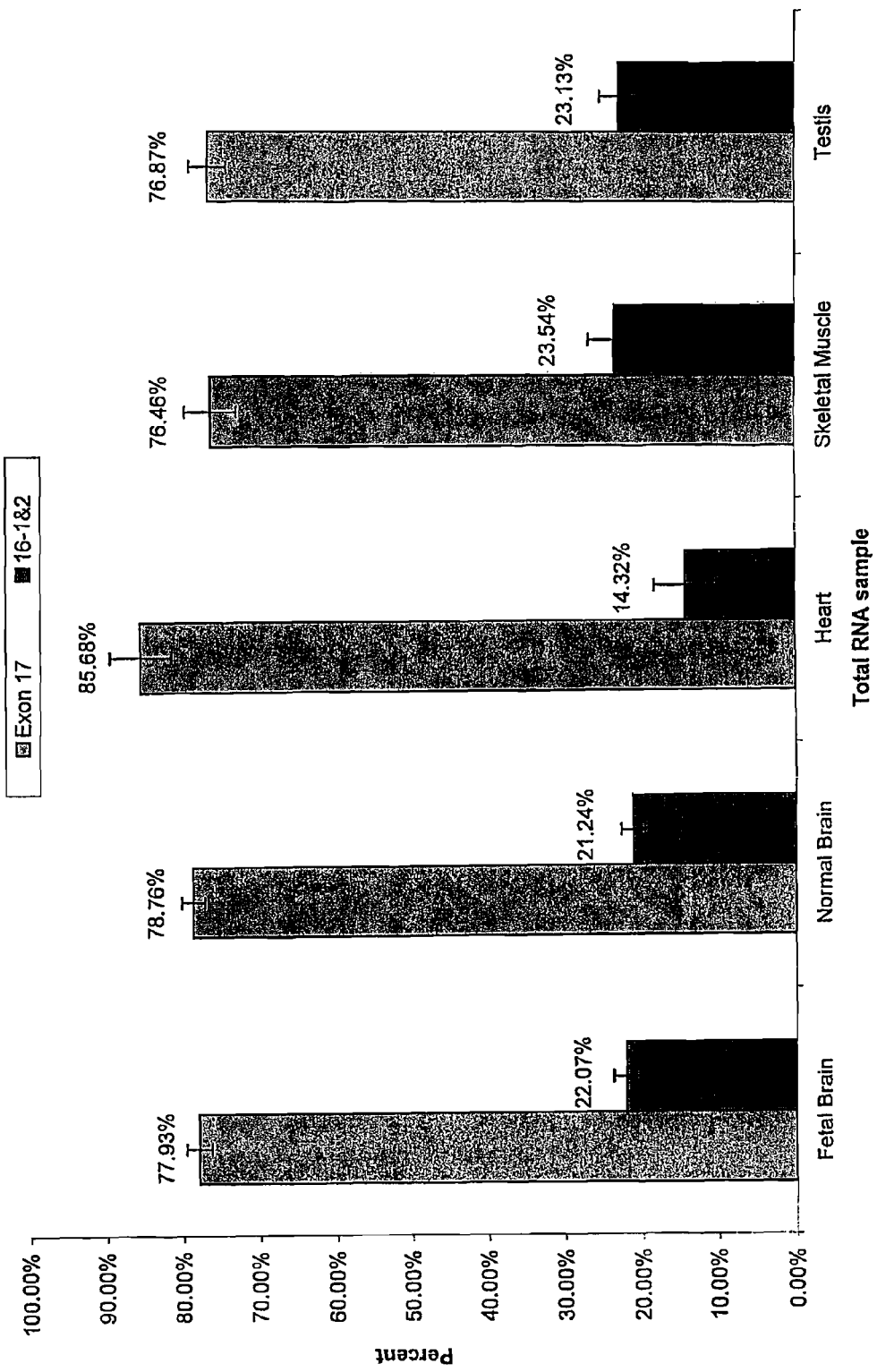
FIG. 7 is a graph depicting the tissue distribution of $BK_{Ca}$ channel intron-containing transcripts that contain 16-1 and 16-2 intronic regions.

Transcripts with 16-1 and 16-2 intronic regions were detected in all tissues, ranging from a low of 14.3% for heart to a high of 23.5% for skeletal muscle (FIG. 7). These transcripts all included exon 17. Regarding alternatively-spliced exons 17a and 17b, transcripts containing exon 17a were not detected in heart or testis (FIG. 8). Exon 17b was detected only in fetal brain and testis (FIG. 9). Transcripts containing: both exons 17a and 17b; only exon 17a; only exon 17b; and neither exon 17a or exon 17b were detected in fetal brain.

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

---

What is claimed is:

1. A method of decreasing the excitability of a neuron, said method comprising administering to the neuron an siRNA molecule specific for intron-containing KCNMA1 mRNA, wherein the administration of the siRNA molecule specific for intron-containing KNCMA1 mRNA decreases the cytoplasmic level of intron-containing KCNMA1 mRNA in the neuron, wherein the decrease in the cytoplasmic level of intron-containing KCNMA1 mRNA causes a decrease in the excitability of the neuron.

2. The method of claim 1, wherein said intron-containing KCNMA1 mRNA comprises intron 16.

3. The method of claim 2, wherein said intron 16-containing KCNMA1 mRNA further comprises exon 17 spliced directly to exon 18.

4. The method of claim 1, wherein decreasing the cytoplasmic level of intron-containing KCNMA1 mRNA causes a change in distribution of $BK_{Ca}$ channels in the neuron.

5. A method of modulating the function of a neuron, said method comprising administering to the neuron an siRNA molecule specific for intron-containing KCNMA1 mRNA, wherein the administration of the siRNA molecule specific for intron-containing KNCMA1 mRNA decreases the cytoplasmic level of intron-containing KCNMA1 mRNA in the neuron, wherein the decrease in the cytoplasmic level of intron-containing KCNMA1 mRNA modulates the function of the neuron.

6. The method of claim 5, wherein the intron-containing KCNMA1 mRNA is dendritically targeted.

7. The method of claim 1, wherein the siRNA molecule specific for intron-containing KCNMA1 mRNA comprises a nucleotide sequence selected from the group consisting of SEQ ID NO:31, SEQ ID NO:32, SEQ ID NO:33 and SEQ ID NO:34.

8. The method of claim 5 wherein the siRNA molecule specific for intron-containing KCNMA1 mRNA comprises a nucleotide sequence selected from the group consisting of SEQ ID NO:31, SEQ ID NO:32, SEQ ID NO:33 and SEQ ID NO:34.

* * * * *

SEQUENCE LISTING

```
<160> NUMBER OF SEQ ID NOS: 40

<210> SEQ ID NO 1
<211> LENGTH: 34
<212> TYPE: DNA
<213> ORGANISM: Artificial Sequence
<220> FEATURE:
<223> OTHER INFORMATION: synthetic oligonucleotide

<400> SEQUENCE: 1
cagacaggtg aggctaatga gggagacgag taat                           34

<210> SEQ ID NO 2
<211> LENGTH: 34
<212> TYPE: DNA
<213> ORGANISM: Artificial Sequence
<220> FEATURE:
<223> OTHER INFORMATION: synthetic oligonucleotide

<400> SEQUENCE: 2
aggatgggag ttgttttgga gtgagaagat gagc                           34

<210> SEQ ID NO 3
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 3
atctgcagac ggaaatgttt gttgtaa                                   27

<210> SEQ ID NO 4
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 4
tgtagtccct ccttccctcc agt                                       23

<210> SEQ ID NO 5
<211> LENGTH: 31
<212> TYPE: DNA
<213> ORGANISM: Artificial Sequence
<220> FEATURE:
<223> OTHER INFORMATION: synthetic oligonucleotide
```

```
<400> SEQUENCE: 5
gtttgcgaaa ctaaagctct taatgatagc c                               31

<210> SEQ ID NO 6
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 6
cttttgggat ctgtgatgtc atcatgg                                    27

<210> SEQ ID NO 7
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 7
tggccgcctg gacggttc                                              18

<210> SEQ ID NO 8
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 8
tgagacactg cgctttcg                                              18

<210> SEQ ID NO 9
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 9
ccactgagtc tgtggagg                                              18

<210> SEQ ID NO 10
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 10
ccagcccagt gaatgacc                                              18

<210> SEQ ID NO 11
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 11
tacacatcca tccatcat                                              18

<210> SEQ ID NO 12
<211> LENGTH: 18
```

```
<212> TYPE: DNA
<213> ORGANISM: Artificial Sequence
<220> FEATURE:
<223> OTHER INFORMATION: synthetic oligonucleotide

<400> SEQUENCE: 12
cagggcccaa acaaaaca                                                 18

<210> SEQ ID NO 13
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 13
gtacaccatc gtcaccat                                                 18

<210> SEQ ID NO 14
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 14
ggcaaaccta gacttccaaa ca                                            22

<210> SEQ ID NO 15
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 15
caacgagcgg acaaacga                                                 18

<210> SEQ ID NO 16
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 16
gcccgatttc taagggataa a                                             21

<210> SEQ ID NO 17
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 17
cacctgcttc actgcctg                                                 18

<210> SEQ ID NO 18
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 18
cccatccctc ctttgctt                                                 18
```

```
<210> SEQ ID NO 19
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 19
acaaggatca gcctgcag                                                 18

<210> SEQ ID NO 20
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 20
tgggaaatgg caaggcta                                                 18

<210> SEQ ID NO 21
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 21
catcagaaca aacagctg                                                 18

<210> SEQ ID NO 22
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 22
agggctgggg gaagttct                                                 18

<210> SEQ ID NO 23
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 23
caccatgtac ctggaggt                                                 18

<210> SEQ ID NO 24
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 24
ccctccttcc cgtttgag                                                 18

<210> SEQ ID NO 25
<211> LENGTH: 18
<212> TYPE: DNA
<213> ORGANISM: Artificial Sequence
<220> FEATURE:
<223> OTHER INFORMATION: synthetic oligonucleotide
```

```
<400> SEQUENCE: 25
agagtaccag ctcttcga                                                 18

<210> SEQ ID NO 26
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 26 gcggggtga agtctctc                                                  18

<210> SEQ ID NO 27
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 27
gaggggcacc actaccttt                                                18

<210> SEQ ID NO 28
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 28
tcccatgtgc tcctgtcc                                                 18

<210> SEQ ID NO 29
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 29
tggactttca tcgattct                                                 18

<210> SEQ ID NO 30
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 30
actgggcatc tgggatga                                                 18

<210> SEQ ID NO 31
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 31
cgagccggag aagag                                                    15

<210> SEQ ID NO 32
<211> LENGTH: 15
```

```
<212> TYPE: DNA
<213> ORGANISM: Artificial Sequence
<220> FEATURE:
<223> OTHER INFORMATION: synthetic oligonucleotide

<400> SEQUENCE: 32
caccccagaa gccag                                                          15

<210> SEQ ID NO 33
<211> LENGTH: 14
<212> TYPE: DNA
<213> ORGANISM: Artificial Sequence
<220> FEATURE:
<223> OTHER INFORMATION: synthetic oligonucleotide

<400> SEQUENCE: 33
cggaggggga agag                                                           14

<210> SEQ ID NO 34
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 34
aaccacacca ggccg                                                          15

<210> SEQ ID NO 35
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 35
taattaaccc tgggaaccac                                                     20

<210> SEQ ID NO 36
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 36
tcctgaagaa tgcccacttg                                                     20

<210> SEQ ID NO 37
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 37
atgtgttggg tgagttcctc                                                     20

<210> SEQ ID NO 38
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 38
tagcctcacc tgtctga                                                        17
```

```
<210> SEQ ID NO 39
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 39
cggttgctca tcttcaa                                                    17

<210> SEQ ID NO 40
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 40
tgtagatgga catcttgg                                                   18
```